(12) United States Patent
Inglese et al.

(10) Patent No.: US 6,335,176 B1
(45) Date of Patent: Jan. 1, 2002

(54) INCORPORATION OF PHOSPHORYLATION SITES

(75) Inventors: James Inglese, Dayton; Joseph Fraser Glickman, Garwood, both of NJ (US)

(73) Assignee: Pharmacopeia, Inc., Cranbury, NJ (US)

( * ) Notice: Subject to any disclaimer, the term of this patent is extended or adjusted under 35 U.S.C. 154(b) by 0 days.

(21) Appl. No.: 09/174,216

(22) Filed: Oct. 16, 1998

(51) Int. Cl.$^7$ ............... C07K 1/113; C07K 1/13; C07K 7/06; C12P 21/00; G01N 33/58

(52) U.S. Cl. ............... 435/7.72; 435/68.1; 530/329; 530/345

(58) Field of Search ............... 530/300, 326, 530/327, 328, 329, 345; 435/7.72, 15, 68.1, 132, 194

(56) References Cited

U.S. PATENT DOCUMENTS

| | | | | |
|---|---|---|---|---|
| 5,106,955 A | * | 4/1992 | Endo et al. | 530/391.1 |
| 5,165,923 A | * | 11/1992 | Thorpe et al. | 424/85.91 |
| 5,459,240 A | * | 10/1995 | Foxwell et al. | 530/328 |
| 5,583,212 A | * | 12/1996 | Foxwell et al. | 536/26.26 |
| 5,599,681 A | * | 2/1997 | Epstein et al. | 435/7.23 |
| 5,986,061 A | * | 11/1999 | Pestka | 530/352 |
| 6,066,462 A | * | 5/2000 | Goueli | 435/7.1 |

OTHER PUBLICATIONS

Pierce Immuno Technology Catalog & Handbook p. A–6, 1992.*

Foxwell et al. Conjugation of Monoclonal Antibodies to a Synthetic . . . Br. J. Cancer, vol. 57, pp. 489–493, 1988.*

Cell Biology: Bo–Liang Li et al., Creation of Phosphorylation Sites in Proteins: Construction of a Phosphorylatable Human Interferon α, *Proc. Natl. Acad. Sci. USA*, vol. 86, pp. 558–562, Jan. 1989.

Michael Brinkley, A Brief Survey of Methods for Preparing Protein Conjugates with Dyes, Haptens, and Cross–Linking Reagents, *Bioconjugate Chem.*, vol. 3, No. 1, 1992, pp. 2–13.

* cited by examiner

Primary Examiner—Jeffrey E. Russel
(74) Attorney, Agent, or Firm—Heslin Rothenberg Farley & Mesiti P.C.

(57) ABSTRACT

A reagent is described for incorporating phosphorylation sites into compounds, particularly into proteins and peptides. The reagent has the structure

A—B—C wherein A is a moiety that is specifically reactive with a reactive side chain in the compound, B is a linking moiety, and C is a peptide sequence that contains a kinase substrate.

16 Claims, 12 Drawing Sheets

$R = H$ $R = PO_3$ a.
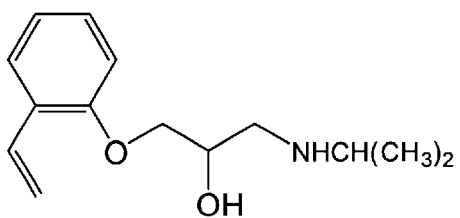
Alprenolol
b.
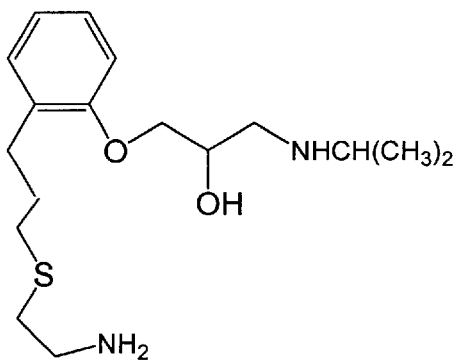
Alprenolol amine
c.
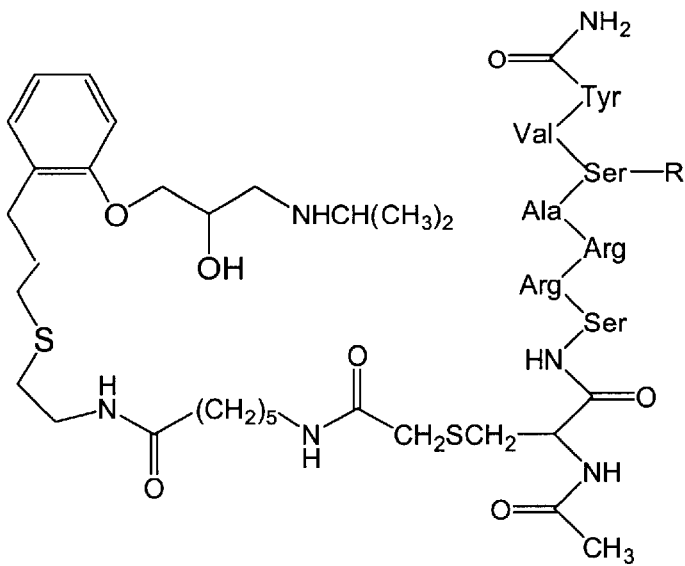
$R = H$
$R = PO_3$
FIGURE 7

| Receptor Class | Ligand Class | Ligand/Receptor Tested | Assay Format* | Ligand sp.act[o] (cpm/fmol) | Signal (cpm$^{33}$P) | | Ligand Bound/Well (fmol) | Signal/ Noise[p] |
|---|---|---|---|---|---|---|---|---|
| | | | | | Total | Nonspecific | | |
| G Protein-Coupled Receptor | peptide | NKA/NK2R[a] | cells[l] | 13 | 201 ± 30 | 10 ± 4 | 15 | 19.4 |
| | peptide | NKA/NK2R[b] | membranes[l] | 13 | 36 ± 4 | 7 ± 3 | 2.2 | 5.3 |
| | chemokine | IL8/CXCR2[c] | cells[l] | 100 | 153 ± 6 | 7.3 ± 0.1 | 1.5 | 21 |
| | antagonist | alprenolol/β$_2$AR[d] | cells[l] | 4000 | 4,568 ± 257 | 847 ± 11 | 1.1 | 5.4 |
| | antagonist | alprenolol/β$_2$AR[e] | membranes[l] | 4000 | 11,895 ± 448 | 1,244 ± 176 | 2.7 | 9.6 |
| Cytokine Receptor | cytokine | Epo/EpoR[f] | plate binding[m] | 112 | 1,367 ± 115 | 226 ± 52 | 12.2 | 6.1 |
| | cytokine | leptin/ObR[g] | plate binding[m] | 135 | 1,888 ± 79 | 278 | 14 | 6.8 |
| | cytokine | leptin/ObR[h] | SPA[n] | 135 | 145,000 ± 7,071 | 29,140 ± 2,273 | 859 | 5 |
| Soluble Binding Protein | biotin | biotin/NeutrAvidin[i] | plate binding[m] | 4000 | 5,641 | 240 | 1.4 | 23.5 |
| | biotin | biotin/NeutrAvidin[j] | SPA[n] | 4000 | 49,285 ± 2,130 | 2,790 ± 197 | 11.6 | 17.7 |

FIGURE 8

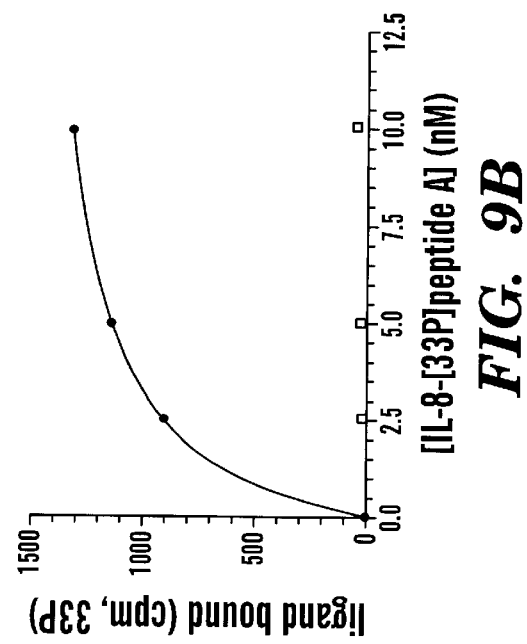
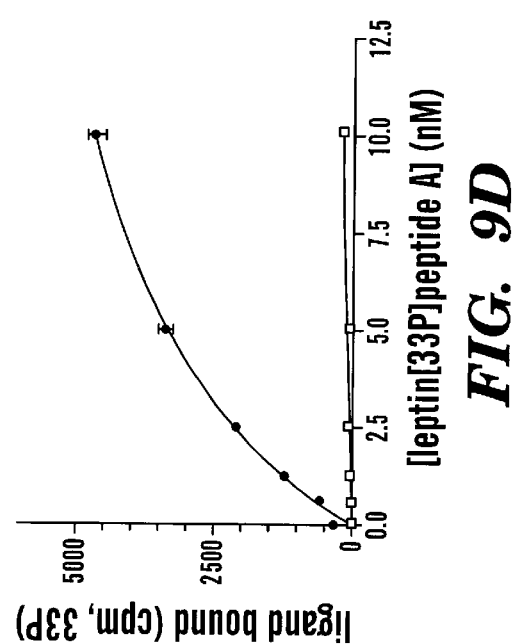
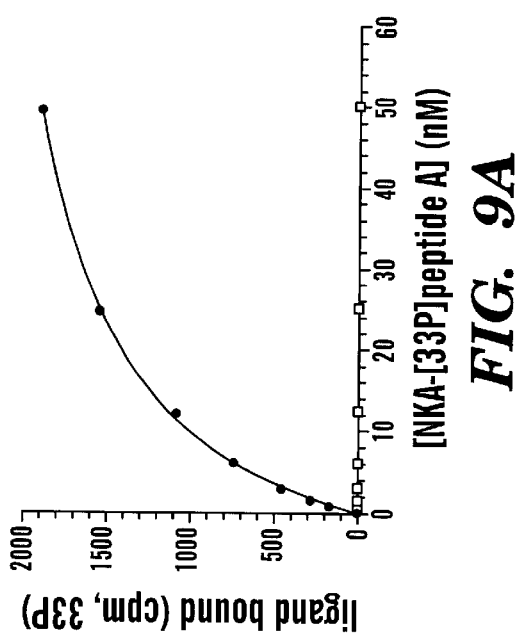
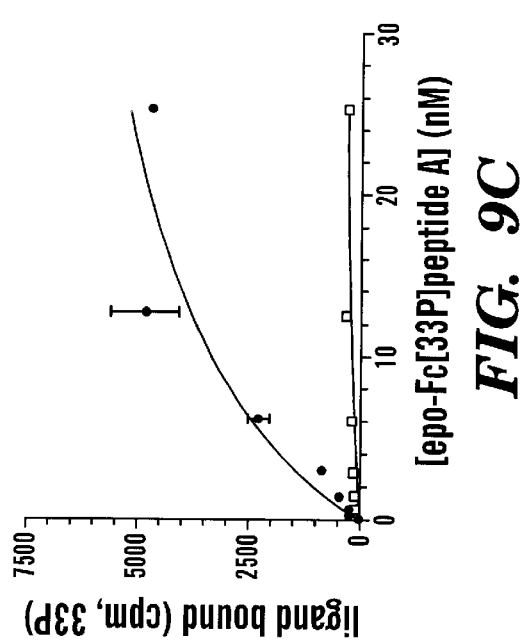
FIG. 9A
FIG. 9B
FIG. 9C
FIG. 9D

| ligand | NKA-[$^{33}$P]phosite | [$^{125}$I]NKA | Ref. | [Eu$^{3+}$]NKA | Ref. |
|---|---|---|---|---|---|
| $K_D$ | 14.5 | 2.6 | d | 1.8 ± 0.12 | h |
| $K_i$(NKA) | 0.8 | 1.9 ± 0.99 | e | 2.0 ± 0.5 | h |
| ligand | IL8-[$^{33}$P]phosite | [$^{125}$I]IL8 | | [Eu$^{3+}$]IL8 | |
| $K_D$ | 1.7 | 2.3 ± 0.8 | f | 2.4 ± 1.1 | f |
| $K_i$(IL8) | 2 | 3.7 ± 2.4 | f | 3.7 ± 2.4 | f |
| ligand | epo-[$^{33}$P]phosite | [$^{125}$I]epo | | [Eu$^{3+}$]epo-Fc | |
| $K_D$ | ND | 0.2 | g | ND | |
| $K_i$(epo-Fc) | 18 | ND | | ND | |
| ligand | leptin-[$^{33}$P]phosite | [$^{125}$I]leptin | | [Eu$^{3+}$]leptin | |
| $K_D$ | 6 | 0.7$^i$ | i | ND | |
| $K_i$(leptin) | 1.7 | 0.6 ± 0.2$^j$ | j | ND | |

FIGURE 10

INCORPORATION OF PHOSPHORYLATION SITES

FIELD OF THE INVENTION

This invention relates to the incorporation in compounds of sites that are substrates for phosphorylating enzymes. The compounds that are phosphorylated by these enzymes, for example proteins and peptides, are particularly useful in assays, such as those used in drug discovery.

BACKGROUND OF THE INVENTION

Ligand binding techniques, which measure molecular interactions, have been fundamental in the elucidation of cellular signaling processes and in the discovery of drugs. As the understanding of the molecular basis of disease has matured, the number of potential molecular targets for pharmaceutical intervention has dramatically increased. As a result, there is a need in the drug discovery process for new methods to measure novel biomolecular interactions. Studies using [$^{125}$I]-ACTH (Lefkowitz et al., (1970) *Proc. Natl. Acad. Sci. U.S.A.* 65(3): 745–752) and [$^{125}$I]-insulin (Cuatrecasas, (1971) *Proc. Natl. Acad. Sci.* 68(6): 1264–8) allowed the direct detection of G protein-coupled receptors and cytokine receptors, respectively, for the first time. These methodologies have since been widely employed in the field of signal transduction biochemistry.

The Bolton-Hunter reagent (Bolton and Hunter, (1973) *Biochem. J.* 133: 529–539) subsequently allowed the introduction of $^{125}$I into proteins using a mild acylation reaction, thus expanding the use of $^{125}$I-labeling to proteins that are sensitive to oxidative iodination. The Bolton-Hunter reagent also allowed labeling of proteins or peptides that lack tyrosine residues by linking to reactive amine groups.

Fluorescent ligands, which allow detection sensitivities to be achieved that are similar to those achieved using $^{125}$I, are now also routinely used (Hemmila and Webb (1997) *Drug Discovery Today* 2:373–381; Inglese et. al. (1998) *Biochemistry* 37:2372–2377. Fluorescent labeling procedures are safer and more stable than radiolabeling procedures employing $^{125}$I.

However, radiolabeled ligands remain useful because of the unique properties of radioisotopes, which allow important assay techniques such as the scintillation proximity assay (Hart and Greenwald (1979) *Mol. Immunol.* 16: 265–267; Bosworth and Towers (1989) *Nature* 341: 167–168) and autoradiography to be carried out. Nevertheless, to employ such assays advantageously, a variety of labeling methods are required.

Phosphorylation reactions can be carried out to introduce radioactive phosphorus into compounds. In proteins, this has been done by incorporating cAMP-dependent protein kinase A (PKA) consensus sites. For example, labeling of receptor ligands and fusion proteins with $^{32}$P has been accomplished by recombinantly engineering PKA consensus sites into the amino acid sequences of those ligands and proteins (Li et al. (1989) *Proc. Natl. Acad. Sci. USA* 86:558–562). Such recombinant methods, however, must be individually designed for each target protein. Furthermore, when the phosphorylation site is recombinantly introduced into the protein sequence it can adversely affect protein function or become inaccessible after the protein has folded. Also, recombinantly introducing the phosphorylation site normally allows only one site to be incorporated.

There is a need for a method to chemically modify already existing proteins and peptides so that they become substrates for protein kinase. Such a method would be used to radioactively phosphorylate proteins that have already been synthesized, such as those that are commonly commercially available.

There is also a need for a method that allows introduction of multiple phosphorylation sites in proteins, and which normally does not interfere with the protein's function, or become inaccessible as a result of protein folding.

SUMMARY OF THE INVENTION

This present invention relates to a reagent for incorporating phosphorylation sites into compounds, particularly into proteins and peptides. The reagent has the structure

A—B—C wherein A is a moiety that is specifically reactive with a reactive side chain in the compound, B is a linking moiety, and C is a peptide sequence that contains a kinase substrate.

The invention also relates to a method involving reacting the reagent with the compound to produce a phosphorylatable product, and phosphorylating the product using a kinase specific for the kinase substrate.

In another aspect, the present invention relates to the phosphorylatable or phosphorylated product resulting from the method of the invention. dr

BRIEF DESCRIPTION OF THE DRAWINGS

FIGS. 7A and 7B, and 7C show the structures of alprenolol (FIG. 7A), an alprenolol derivative (FIG. 7B) and the alprenolol derivative modified with the reagent of the invention (FIG. 7C).

FIG. 8 shows Table 1, containing results for ligand-receptor systems assayed using compounds labeled according to the invention.

FIG. 9 shows results of saturation binding experiments for four ligands labeled with the reagent of the invention.

FIG. 10 is a Table (Table 2) showing the estimated dissociation ($K_D$) and inhibition ($K_i$) constants determined for four ligands based on results shown in FIG. 9 and FIG. 11. The calculated constants are compared with published values for the corresponding $^{125}$I or $Eu^{3+}$-labeled ligands.

Figure 1:
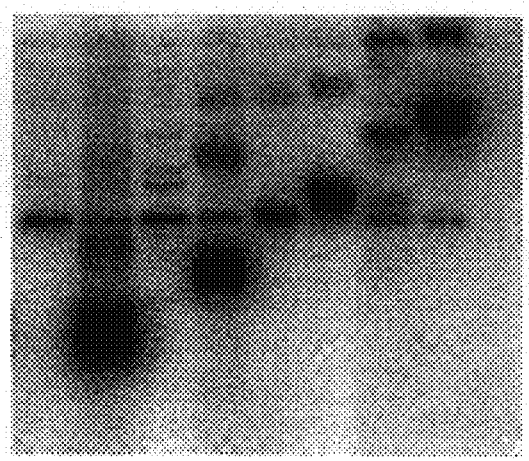
FIG. 1A shows a coomassie stained gel of proteins either treated (lanes 2,4,6,8) or untreated (lanes 1,3,5,7) with the reagent of the invention and phosphorylated with PKA using [γ-$^{32}$P]ATP.
FIG. 1B shows the same gel exposed to a phosphoimager screen to detect [$^{32}$P] incorporation.

reactive amines include N-hydroxysuccinimide (NHS) esters and isothiocyanates. Moieties useful for reacting with thiols include haloacetyl derivatives (e.g., an iodoacetamide), maleimides, and pyridyl disulfides. The use of such moieties and conditions employed to react such moieties with reactive side groups, are described, for example, in Brinkley, *Bioconjugate Chem.* 1992, 3:2–13.

Linking groups useful in the invention include, but are not limited to, those derived from commonly used bifunctional linking reagents. In particular, commonly available cross-linking reagents can be employed to obtain the reactive moiety linked to a peptide containing a kinase substrate. For example, bismaleimidohexane (BMH) can be reacted with the sulfhydryl group of a peptide containing a kinase substrate sequence to obtain the reagent of the invention. The resulting compound, for example, could have the following structure where the kinase substrate employed is the kinase A substrate sequence:

(SEQ ID NO. 6)

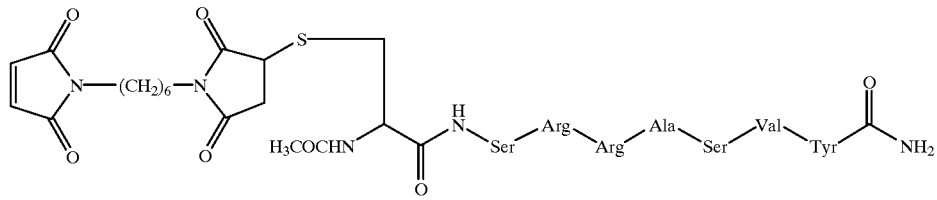

DETAILED DESCRIPTION OF THE INVENTION

All publications, patents, and patent applications referred to herein are hereby incorporated by reference in their entireties.

The present invention relates to methods and reagents for introducing a substrate for a kinase into a compound, and for phosphorylating the resulting product. The invention also relates to the resulting unphosphorylated, and phosphorylated products.

The method allows compounds having reactive side chains to be radioactively phosphorylated without the need to carry out recombinant methods to incorporate an amino acid sequence that is a kinase substrate. Instead, the reagent of the invention links a kinase substrate sequence to a pre-existing compound, such as a previously synthesized protein. The method is highly adaptable, and can be used to phosphorylate a broad variety of compounds that contain reactive side groups.

The reagent of the invention avoids production of proteins having an inaccessible kinase substrate sequence, as can result using known recombinant methods. Instead, the reagent of the invention reacts with surface accessible amino acids, providing phosphorylation sites that are accessible to the kinase.

Furthermore, using the reagent of the invention, multiple phosphorylation sites can be incorporated merely by increasing the ratio of reagent to protein. This allows labeled products to be obtained that have a higher specific activity than is normally obtained with recombinant methods. For example, using the method of this invention proteins have been obtained exhibiting a high specific activity of approximately 2000 Ci/mmol.

Preferably, the reactive side group contained in the compound to be phosphorylated is an amine or a thiol group. Such reactive side groups are commonly found in proteins and polypeptides.

The reagent of the invention contains a moiety for reacting with the reactive side group. Moieties for reacting with This reagent can be used to conjugate a phosphorylation site to a reactive thiol of a protein to be labeled.

Following are examples of other linking agents that can be used to produce reagents of the invention by reacting the linking agent with a peptide containing a kinase substrate sequence: 1,4di-[3-(2-pyridyldithio)-propionamido]butane (DPDPB); N-γ-maleimidobutyryloxysuccinimide ester (GMBS); N-γ-maleimidobutyryloxysulfosuccinimide ester (Sulfo-GMBS); m-maleimidobenzoyl-N-hydroxysuccinimide ester (MBS); N-hydroxysuccinimidyl-2,3-dibromopropionate (SDPB); m-maleimidobenzoyl-N-hydroxysulfosuccinimide ester (Sulfo-MBS); N-succinimidyl[4-iodoacetyl]aminobenzoate (SIAB); sulfosuccinimidyl[4-iodoacetyl]aminobenzoate (Sulfo-SIAB); succinimidyl 4[N-maleimidomethyl]cyclohexane-1-carboxylate (SMCC); sulfosuccinimidyl-4[N-maleimidomethyl]cyclohexane-1-carboxylate (Sulfo-SMCC); succinimidyl 4-[p-maleimidophenyl]butyrate (SMBP); sulfosuccinimidyl 4-[p-maleimidophenyl]butyrate (Sulfo-SMBP); 4-succinimidyloxycarbonylmethyl-α-[2-pyridyldithio]toluene (SMPT); sulfosuccinimidyl-6-[α-methyl-α-(2-pyridyldithio)toluamido]hexanoate (Sulfo-SMPT); N-succinimidyl-3-[2-pyridyldithio]propionate (SPDP); succinimidyl 6-[3-(2-pyridyldithio)propionamido] hexanoate (LC-SPDP); sulfosuccinimidyl 6-[3-(2-pyridyldithio)propionamido]hexanoate (Sulfo-LC-SPDP); succinimidyl 6-[(iodoacetyl)amino]hexanoate (S-1666) and succinimidyl 6-[6-[[(iodoacetyl)amino]hexanoyl]amino] hexanoate (S-1668). These reagents, among many other well-known linkers, are commercially available, for example, from Pierce (Rockford, Ill.) and Molecular Probes, Inc. (Eugene, Oreg.).

Examples of reagents of the invention resulting from conjugation of bifunctional linkers to a peptide containing a kinase substrate sequence are shown below, where the kinase substrate sequence is a cyclic AMP (cAMP)—dependent protein kinase (PKA) substrate sequence.

(SEQ ID NO. 6)
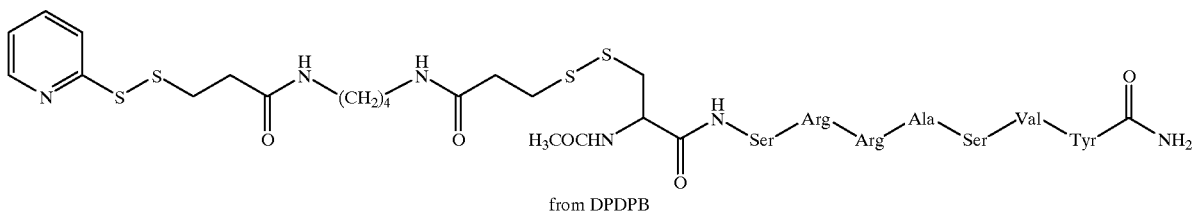
from DPDPB
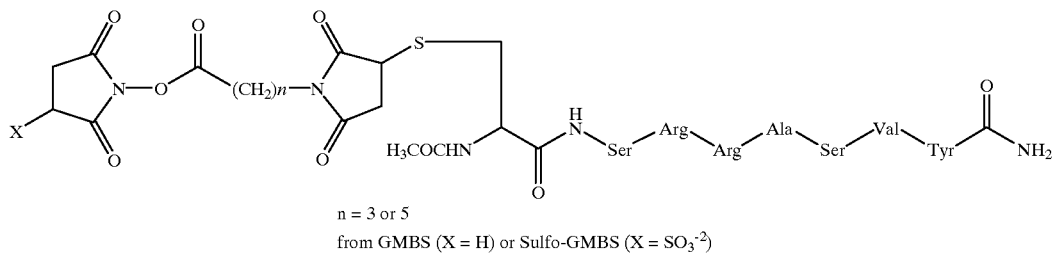
n = 3 or 5
from GMBS (X = H) or Sulfo-GMBS (X = SO$_3^{-2}$)
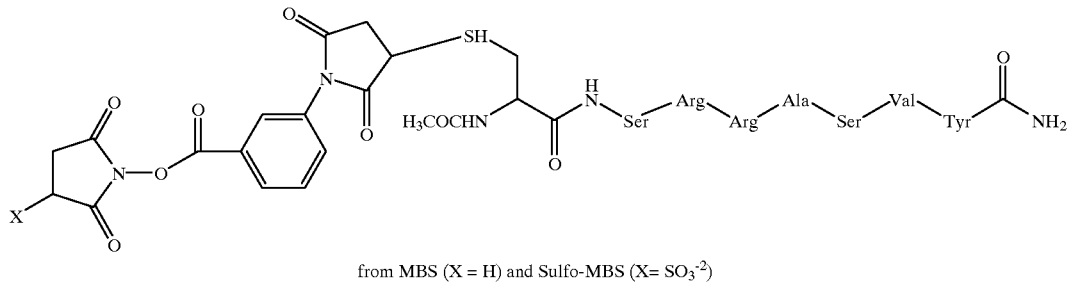
from MBS (X = H) and Sulfo-MBS (X = SO$_3^{-2}$)
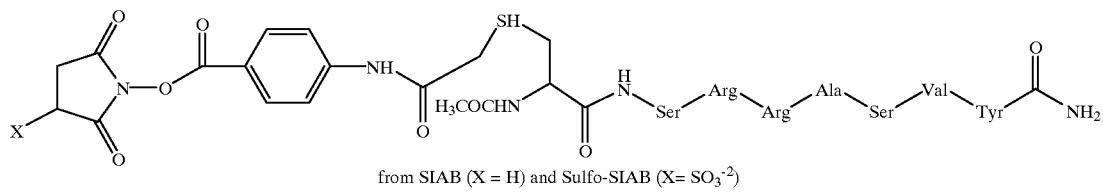
from SIAB (X = H) and Sulfo-SIAB (X = SO$_3^{-2}$)
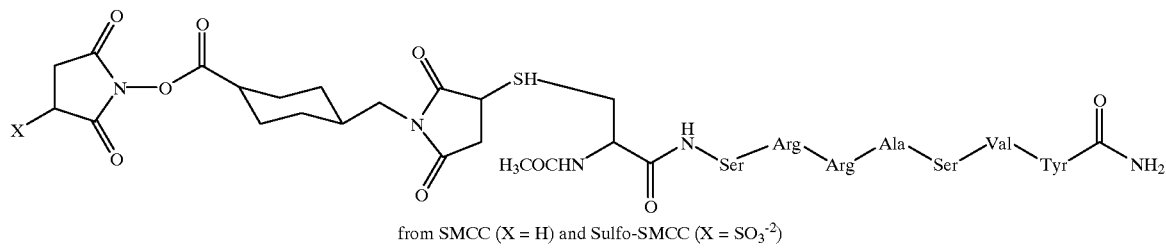
from SMCC (X = H) and Sulfo-SMCC (X = SO$_3^{-2}$)
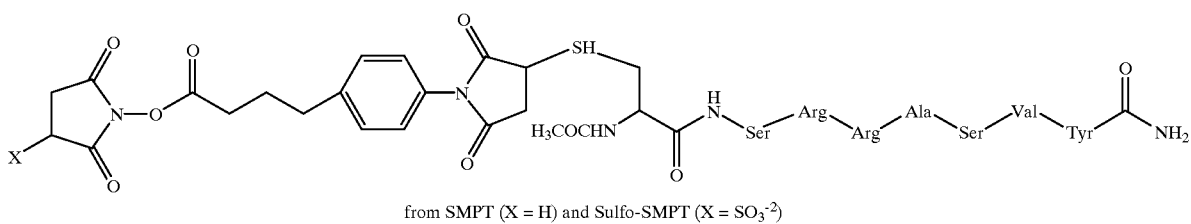
from SMPT (X = H) and Sulfo-SMPT (X = SO$_3^{-2}$)

-continued

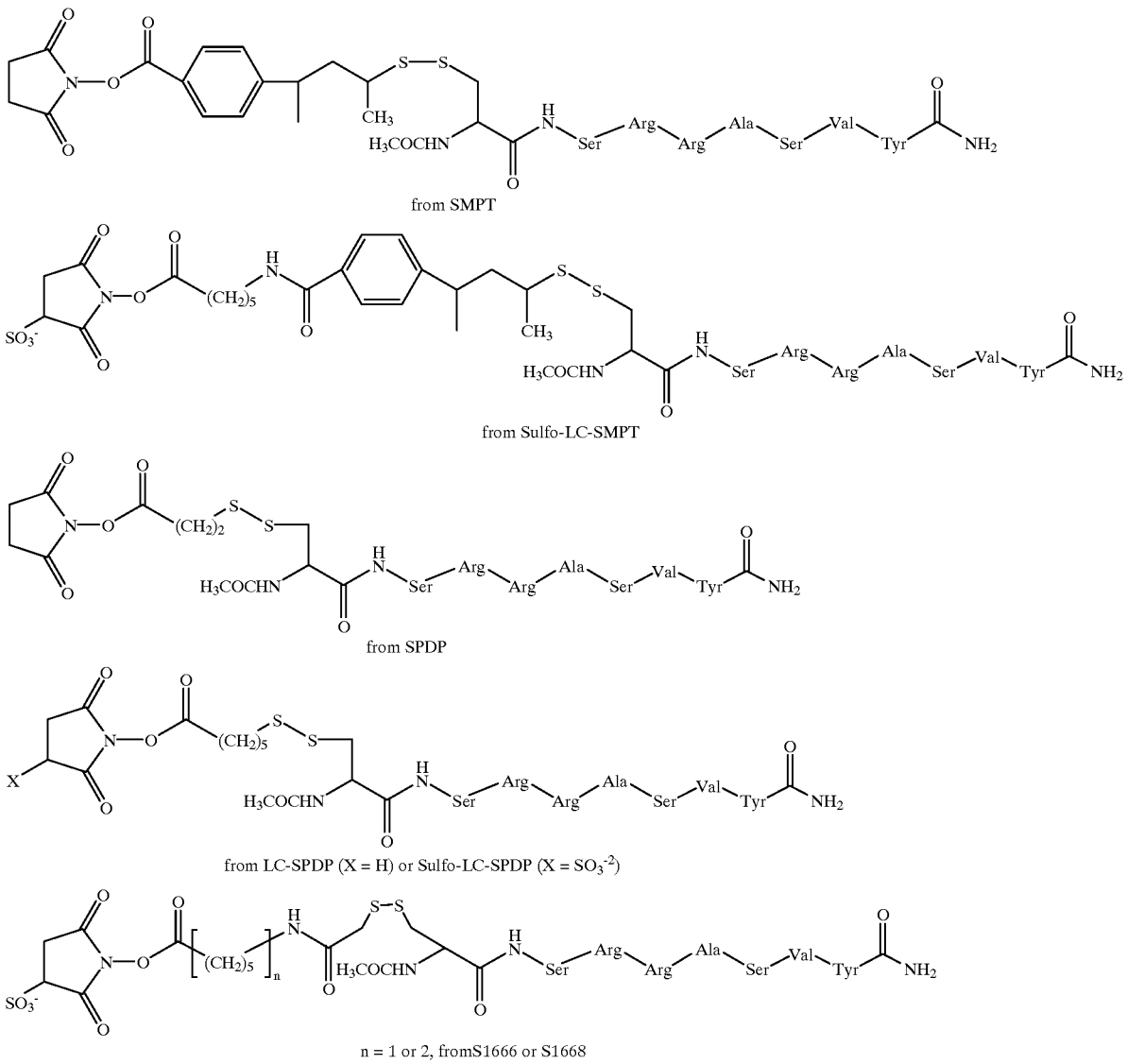

n = 1 or 2, fromS1666 or S1668

Where necessary to avoid linking of both sides of homobifunctional reagent with the peptide containing the substrate sequence, the reagent can be reacted in excess.

The preferred reagent employed in the present invention contains an NHS ester, such as is contained in the Bolton-Hunter reagent commonly employed to introduce radioactive iodine labels onto reactive amines of lysines. The succinimidyl moiety of such reagents combines with amine groups in a mild acylation reaction.

While the succinimidyl moiety employed in Bolton-Hunter reagents is often sulfonated in order to increase solubility, the reagent of the invention often need not be because the peptide sequence helps solubilize the reagent in water, eliminating the need for such substitutions. Nevertheless, if desired, substituents, e.g., $SO_3Na$, can be employed.

Peptide substrate sequences for kinases that can be incorporated in the reagent of the invention are well-known in the art. In one embodiment, the sequence is SRRASVY (SEQ ID NO. 1), and the kinase employed in the phosphorylation reaction is protein kinase A (PKA). Another suitable peptide substrate is the "Kemptide" sequence, LRRASLG (SEQ ID NO. 2), which is also a substrate for protein kinase A. Other substrate sequences include KVEKIGEGTYGVVYK (SEQ ID NO. 3), pGluGPWLEEEEEAYGWMDF (SEQ ID NO. 4), and RRLIEDAEYAARG (SEQ ID NO. 5), all of which are substrates for various tyrosine kinases. These peptides, among many other well-known kinase substrates, can be synthesized using conventional methods, or purchased commercially from, e.g., Pierce (Rockford Ill.).

Kinases that can be used to phosphorylate their respective peptide substrate sequences include protein kinase A, tyrosine kinase, cAMP-dependent protein kinase, casein kinase I, casein kinase II, glycogen synthase kinase 3, $p34^{cdc2}$-cyclin B protein kinase, calmodulin-dependent protein kinase II, mitogen-activated protein kinase, cGMP-dependent protein kinase, phosphorylase kinase, Abl tyrosine kinase, and epidermal growth factor receptor kinase. Such kinases are commercially available, and can be obtained from, for example, Calbiochem-Novabiochem Corp. (La Jolla, Calif.), New England Biolabs Inc. (Beverly, Mass.), or Promega Corp. (Madison, Wis.).

Where the reactive moiety is an NHS ester, the succinimidyl moiety is preferably linked to the kinase substrate through linkage of a cysteine thiol located at the amino terminus of the kinase substrate with an acetamide moiety, preferably by reaction with iodoacetamide. The acetamide moiety is conjugated by a spacer region to the succinimidyl moiety. The spacer region preferably contains more than 3 carbon atoms, most preferably more than 5 carbon atoms.

While the reagent of the invention can be employed to phosphorylate proteins and peptides, it can also be used to phosphorylate small molecules containing reactive groups. For example, the reagent can be used to conjugate a phosphorylation substrate sequence to biotin ethylenediamine. The resulting compound is useful for linking a phosphorylation substrate sequence to an avidin containing structure, such as a streptavidin coated bead or microtiter plate. The labeled derivative can be detected, e.g., in a homogeneous assay or plate binding assay.

According to the method of the invention, the reagent of the invention is reacted (or conjugated) with the compound to be phosphorylated under conditions that are suitable with respect to the peptide reactive group contained in the reagent. Such conditions are generally known to those in this art. They are particularly well-known, for example, with respect to commercially available bifunctional reagents, such as those described above. Commercial manuals, such as those provided by Molecular Probes, Inc. (Eugene, Oreg.) provide details of such conditions. Such conjugation methods are also described in Brinkley, *Bioconjugate Chem.* 1992, 3:2–13. Those that are well-known for the Bolton-Hunter reagent can be applied to use of reagent of the invention containing an NHS ester.

Once the reagent has been conjugated to the desired compound containing a reactive side chain, phosphorylation takes place under conditions well known in the art. See Pearson, R. B. and Kemp. B. E. *Methods Enzymol.* 1991, 200:62–81.

In an embodiment of the invention described in the Examples below, [N-acetyl-cys((succinimidyl-6-(thioacetyl) amino) hexanoate)-ser-arg-arg-ala-ser-val-tyr-amide] (SEQ ID NO. 6) is employed to introduce a PKA consensus peptide onto a primary or secondary amine. Formation of this reagent is based on the preferential reactivity of a cysteine thiol located at the amino terminus of the PKA consensus peptide with the electrophilic iodoacetamide moiety of the heterobifunctional crosslinking reagent, succinimidyl 6-((iodoacetyl)amino) hexanoate (SIAX). Coupling conditions in aqueous buffer are described below which allow the succinimidyl ester (NHS ester) to remain intact for a time sufficient for the coupled product to be purified by reverse phase HPLC. The product recoverable by this process is stable as a lyophilized dessicated powder.

Proteins, peptides and small molecules can be acylated with the reagent of the invention. This reagent can be particularly advantageous where the water solubility of the reagent allows coupling reactions to be carried out in completely aqueous systems.

Results described in the Examples section using kinase to phosphorylate ligands conjugated to a kinase substrate according to the invention indicate that substantially complete conversion to the phosphorylated ligand is possible. Furthermore, the invention has been found to allow sensitive detection through $^{33}$P-labeling.

$^{33}$P is preferred for radioligand binding assays using phosphorylated proteins of the invention because it has a half-life nearly double that of $^{32}$P (in particular about 25.4 days vs. 14.3 days) and is safer to use than $^{32}$P.

It is possible to modify the reagent of the invention to incorporate other labels. For example, the peptide containing the kinase substrate can be modified to include a moiety that can be labeled with [$^{3}$H]. A well known example of such a moiety is 3,4-dehydroproline. It is also possible to incorporate a moiety that can labeled with [$^{125}$I], such as a tyrosine amino acid.

The method and reagent of the invention are useful in many types of assays. For example, they can used to detect compounds used in receptor binding assays, such as G protein-coupled receptor binding assays. Preferably, they are used in such assays as part of a high throughput screening to determine candidate drug compounds from a library of potentially active agents.

It is preferred to use the phosphorylated compounds of the invention in a scintillation proximity assay. In this type of assay, radioactive proteins of interest, such as radiolabeled cytokine or ligand, excite scintillant on a bead when they bind to the bead. A homogeneous assay of this type is described in U.S. Pat. No. 4,568,649, employing beads that are impregnated with scintillant (these are commercially sold as Scintillation Proximity Assay beads (SPA™, Amersham Corp., Arlington Heights, Ill.)). The beads are also coated with a ligand that is capable of binding with radio-labeled target in a sample. When the ligand binds to the radio-labeled target, the scintillant on the bead is activated by the radiolabel. The level of light energy produced by the scintillant indicates the amount of bound labeled target in the sample. Use of $^{33}$P labeled protein in such an assay is described in Baum et al., (1996) *Analytical Biochemistry* 237: 129–134.

Most preferably, the method of the invention is carried out as part of a high throughput screening of a library of compounds. Thus, in one embodiment of the invention, the method is carried out with a plurality of compounds to be screened, preferably at least about 96 compounds, such as when using a 96 well microtitre plate. Such assays can also be performed in higher density microtitre plates, such as the 1536 well plate described in U.S. patent application Ser. No. 60/037,636, filed Feb. 18, 1997. The library of compounds to be screened can be quite large, e.g., containing more than 100,000 compounds.

It is preferred that the compounds assayed in the high throughput method be derived from combinatorial libraries on polymer beads. By synthesizing sufficient compound on each bead for a few assays, compound handling is reduced or eliminated.

Using combinatorial libraries prepared on beads, the identity of active compounds is preferably determined using the encoding system described in U.S. Pat. Nos. 5,721,099 and 5,565,324. In this system, chemical tags encoding the identities of the compounds are applied to the solid supports. The identity of the compound on a given support can be determined by detaching the chemical tags from the support, identifying the tags by, e.g., gas chromatography, and correlating the identities of tags with the identity of the compound. Once an active compound is identified, the corresponding bead (which had contained the compound) can be examined, and the identity of the compound determined by releasing the tags and decoding by this method.

The invention is further illustrated by the examples shown below, which are intended to merely exemplify the invention, and not to be interpreted as limiting its scope.

EXAMPLES

Materials

A peptide containing a substrate sequence for protein kinase A [AcNH]CSRRASVY[NH$_2$] (SEQ ID NO. 6) (peptide A) was obtained from Princeton Biomolecules (Columbus, Ohio). Neurokinin A (NKA) was obtained from Penninsula Laboratories (Belmont, Calif.). Succinimidyl 6-((iodoacetyl)amino)hexanoate (SIAX) and biotin ethylenediamine were obtained from Molecular Probes (Eugene, Oreg.). Molecular weight standards were obtained from Boehringer Mannheim (Mannheim, Germany). Protein Kinase A was obtained from Promega (Madison, Wis.). [$^{33}$P]ATP and [$^{32}$P]ATP were obtained from Life Science/NEN (Boston, Mass.). Protein A Sepharose CL4B was obtained from Amersham-Pharmacia (Piscataway, N.J.). Streptavidin SPA beads were obtained from Amersham-Pharmacia. SDS-PAGE analysis was carried out using NuPAGE™ precast gels (Novex (San Diego, Calif.). Dulbecco's Eagle Modified medium (DMEM), fetal bovine serum (FBS) and all media supplements were obtained from Gibco (Gaithersburg, Md.). All solvents were of HPLC grade (Fisher, Springer, N.J.).

Methods

HPLC. Reverse phase chromatography was performed on a Dynamax HPLC system (Rainin, Emeryville, Calif.) using an acetonitrile/water/TFA gradient where solvent A was water containing 0.1% TFA and solvent B was 90% acetonitrile containing 0.1% TFA. The column (Jupiter 300 Å, 5 um, C5, 250×4.6 mm, Phenomenex, Torrance, Calif.) was developed using one of the following 30 min. linear gradients: condition A, 0–30% solvent B; condition B, 0–60% solvent B; or condition C, 0–100% solvent B. Samples ranging from 1–150 nmol of material were diluted with 0.2 ml solvent A prior to injection and separations were monitored at both 214 and 280 nm. For samples <100 pmol, fluorescence detection ($I_{EX}$=220 nm and $I_{Em}$=304 nm) was employed. For purification, peaks of interest were collected by hand, flash-frozen and dried on a Speed Vac (Savant Instruments, Farmingdale, N.Y.) at ambient temperature. Dried samples were stored desiccated at −20° C.

Electrospray Mass Spectrometry. Mass spectrometry was performed in full scan mode using an ion trap mass spectrometer (Model LCQ, Finnigan, San Jose, Calif.), equipped with a pneumatically assisted electro-spray ionization (ESI) source. The scan range was 200–1800 m/z with a 50 msec injection time and 3 microscans per scan. The capillary voltage was 23V and the capillary temperature was 250° C. Samples (10–20 pmol) were injected in a 10–20 ul volume in 50% acetonitrile/1% acetic acid using an HPLC pump (flow rate 0.2 ml/min).

Synthesis of (N-acetyl-cys((succinimidyl-6-(thioacetyl) amino)hexanoate)-ser-arg-arg-ala-ser-val-tyr-amide) (SEQ ID NO. 6). To 0.1 ml of 10 mM peptide A in water was added 0.3 ml of 10 mM SIAX in acetonitrile. To this solution was added 0.15 ml of 200 mM sodium phosphate, pH 6.0. The final concentrations of peptide A and SIAX were 1.8 mM and 5.4 mM, respectively. This reaction was allowed to stand at ambient temperature for 18 hrs after which time unreacted SIAX was extracted with 0.5 ml chloroform. The aqueous phase containing the product of the reaction ("NHS ester") was purified by reverse phase HPLC, condition A; $t_r$ (peptide) 18.5 min.; $t_r$ (SIAX) 23 min.; $t_r$ (NHS ester) 25.5 min. ES-MS, (m/z, observed) 1250.6 (M+H$^+$), 626.9 (M+2H$^+$); (calculated) 1250.7 amu, (predicted) 1250.3 amu. Concentrations were determined by comparison of the peak area from the HPLC trace at 280 nm absorbance with the peak area of a known quantity of N-acetyl-tyrosine ethyl ester or by using the extinction of the NHS ester in 50 mM phosphate buffer, pH 6.5, e=7.5×10$^3$ M$^{-1}$ cm$^{-1}$ at 260 nm (Partis (1983) J. Prot. Chem. 2(3): 263–277).

General Synthesis and Purification Methods for Proteins, Peptides and Small Molecules Coupled to Kinase Substrate. The reactive amine-containing protein, peptide or small molecule of interest was dialyzed against or dissolved in 50 mM NaHCO$_3$, pH 8.3, 0.9% NaCl (coupling buffer) at a concentration of ~1 mg/ml. NHS ester was dissolved in water so that one-tenth volume was added to the protein, peptide, or small molecule resulting in NHS ester: amine ratios greater or less than unity depending on the modification stoichiometry desired. After mixing, the reaction was incubated at room temperature for 18 hr., although the reaction is believed to have been completed within an hour. Conjugates of NHS ester with the compound of interest were purified by reverse phase HPLC, gel-filtration chromatography, microdialysis or protein A affinity chromatography depending on the compound modified.

Phosphorylation Reactions. Reactions (20–100 ml) were conducted containing 40 mM Tris HCl, pH 8.0, 20 mM magnesium acetate (kinase buffer), bioconjugates of NHS ester and compound (2–20 mM), ATP (0–100 mM, Gibco) supplemented with [g-$^{33}$P]ATP or [g-$^{32}$P]ATP to give a final specific activity of 0–1600 Ci/mmol (~0–3520 cpm/fmol). Reactions were initiated by the addition of the catalytic subunit of cAMP-dependent protein kinase (20–100 units, Promega) and incubated at 37° C. for two hr. Highest specific activity labeling reactions used carrier-free [g-$^{33}$P] ATP or [g-$^{32}$P]ATP having stock concentrations of 5 uM.

Specific Preparations. Methods for preparation, purification and characterization of conjugates of the reagent of the present invention with various compounds are described below.

Neurokinin A-peptide A conjugate (N-α-acetyl-S-[NKA-lyS$_2$N$^\epsilon$-amido-(6-aminothioacetyl)hexonyl]cys-ser-arg-arg-ala-ser-val-tyr-amide (SEQ ID NO. 6); NKA-lys$_2$ N$^\epsilon$-peptide A)

A 50 ul aliquot of 2 mM NKA (100 nmol) in coupling buffer was added to an eppendorf tube containing ~40 nmol of peptide A NHS ester powder, vortexed and allowed to stand at ambient temperature for 18 hrs. The conjugate was purified from unreacted NKA by reverse phase HPLC, condition B; $t_r$ (NKA-lys$_2$N$^\epsilon$-peptide A) 22.3 min. ES-MS, (m/z, observed) 1135.2 (M+2H$^+$); 757, 0(M+3H$^+$); (calculated) 2268.2 amu, (predicted) 2267.6. Edman degradation results: cycle 1, His-PTH (phenylthiohydantoin), NKA (4.1 pmol), NKA-lys$_2$N$^\epsilon$-peptide A (3.8 pmol); cycle 2, Lys-PTH was recovered only for NKA (6.9 pmol); cycle 3, Thr-PTH (phenylthiohydantoin), NKA (5.5 pmol), NKA-lys$_2$N$^\epsilon$-peptide A (13.5 pmol); cycles 4, 5, and 6 recovered asp, ser and phe, respectively, for both NKA and NKA-lys$_2$N$^\epsilon$-peptide A.

Neurokinin A-[$^{33}$PO$_3$]peptide A conjugate (N-α-acetyl-S-[NKA-lys$_2$N$^\epsilon$-amido-(6-aminothioacetyl)hexonyl]cys-ser-arg-arg-ala-[$^{33}$PO$_3$]phosphoser-val-tyr-amide (SEQ ID NO. 7); NKA-lys$_2$N$^\epsilon$-[$^{33}$PO$_3$]peptide A). A 100 ul reaction containing two nmol of the NKA-lys$_2$N$^\epsilon$-peptide A (20 uM), 100 U PKA, 10 nmol ATP (100 uM), 0.1 nmol [g-$^{33}$P]ATP (1 uM, 1600 Ci/mmol) in kinase buffer was allowed to proceed at 37° C. for 2 hr. The specific activity of this ATP/[g-$^{33}$P] ATP mixture was ~36 cpm/fmol. The phosphorylated peptide was separated from the non-incorporated [g-$^{33}$P]ATP on reverse phase HPLC, condition B; $t_r$ ([g-$^{33}$P] ATP) ~4 min.; $t_r$ (NKA-lys$_2$N$^\epsilon$-[$^{33}$PO$_3$]peptide A) 22.7 min. ES-MS, (m/z, observed) 1174.7 (M+2H$^+$), 783.6 (M+3H$^+$); (calculated) 2347.6 amu, (predicted) 2347.6 amu.

Interleukin-8-peptide A conjugate (N-α-acetyl-S-[IL8-amido-(6-amino thioacetyl)hexonyl]cys-ser-arg-arg-ala-ser-val-tyr-amide$_{1-4}$(SEQ ID NO. 6); IL8-peptide A$_{1-4}$; IL8-[$^{33}$PO$_3$]peptide A$_{1-4}$). A 200 ul aliquot (200 uM; 40 nmol) of Interleukin-8 was dialyzed against coupling buffer prior to addition to an eppendorf tube containing ~100 nmol of peptide A NHS ester, vortexed and allowed to stand at ambient temperature for 18 hrs. The conjugate was purified by reverse phase HPLC as a mixture of IL8-peptide A conjugates containing between one and four peptide A modifications per IL8, condition B; $t_r$ (IL8) 25.7 min, sharp peak.; $t_r$ (IL8-peptide A) 25.7 min., broader peak. ES-MS (amu): observed (predicted) 9516.8±1 (9517.7) IL8-peptide A; 10651.8±1 (10652.7) IL8-peptide $A_2$; 11787.5±0.84 (11787.7) IL8-peptide $A_3$; 12927.5±8.18 (12922.7) IL8-peptide $A_4$.

Interleukin-8-[$^{33}PO_3$]peptide A conjugate (N-α-acetyl-S-[IL8-amido-(6-aminothioacetyl)hexonyl]cys-ser-arg-arg-ala-[$^{33}PO_3$]phosphoser-val-tyr-amide$_{1-4}$(SEQ ID NO. 7); IL8[$^{33}PO_3$]peptide $A_{1-4}$). A 100 ul reaction containing two nmol IL8-peptide $A_{1-4}$ (20 uM), 100U PKA, 3 nmol ATP (30 uM), 0.25 nmol [g-$^{33}P$]ATP (2.5 uM, 1600 Ci/mmol) in kinase buffer was allowed to proceed at 37° C. for 2 hr. The specific activity of this ATP/[g-$^{33}P$]ATP mixture was ~270 cpm/fmol. The phosphorylated protein was separated from the non-incorporated [g-$^{33}P$]ATP on reverse phase HPLC, condition B; $t_r$ ([g-$^{33}P$] ATP) ~4 min.; $t_r$ (IL8-[$PO_3$]peptide A) 26.6–26.7 min., unresolved doublet. ES-MS (amu): observed (predicted) 9595.1±1.3 (9597.6) IL8-[$PO_3$]peptide A; 10809.5±2.1 (10812.5) IL8-[$PO_3$]peptide $A_2$; 12027.9±0.4 (12027.4) IL8-[$PO_3$]peptide $A_3$.

Leptin-peptide A conjugate (N-α-acetyl-S-[leptin-amido-(6-aminothioacetyl)hexonyl]cys-ser-arg-arg-ala-ser-val-tyr-amide$_{1-2}$ (SEQ ID NO. 6); Leptin-peptide $A_{1-2}$. Leptin (160 ul; 156 uM) was dialyzed against coupling buffer and divided into 4×40 ul aliquots (6.24 nmol each). Varying volumes of peptide A NHS ester (dissolved in water just prior to use to a concentration of ~1.4 nmol/ul) was added to each tube such that the ratio (mol/mol) of leptin:peptide A was 1:0; 1:0.5, 1:1 and 1:5. Water was added to equalize volumes to 62 ul each. Samples were allowed to stand at ambient temperature for ~18 hr. Based on SDS-PAGE analysis of the reactions the 1:5 stoichiometry reaction was chosen for the following characterization. ES-MS (amu): observed (predicted) 16154.6±1.4 (16158.1) leptin: 17292.5±11 (17293.1) leptin-peptide A; 18430.8±7.0 (18428.1) leptin-peptide $A_2$.

Leptin-[$^{33}PO_3$]peptide A conjugate (N-α-acetyl-S-[leptin-amido-)6-aminothioacetyl)hexonyl]cys-ser-arg-arg-ala-[$^{33}PO_3$]phosphoser-val-tyr-amide$_{1-2}$ (SEQ ID NO. 7); Leptin-[$^{33}PO_3$]peptide $A_{1-4}$. A 24 ul reaction containing 60 pmol leptin-peptide $A_{1-2}$ (100 uM), 116 U PKA and 0.25 umol [γ$^{33}P$]ATP (2.5 uM, 1600 Ci/mmol) in kinase buffer was allowed to proceed at 37° C. for 2 hr. The phosphorylated protein was separated from the non-incorporated [γ$^{33}P$] ATP on reverse phase HPLC, condition C; $t_r$ ([γ$^{33}P$] ATP) ~4 min; $t_r$ (leptin-[$PO_3$]peptide A) 23.8 min., broad peak.

Erythropoietin-murine-Fc-peptide A conjugate (N-α-acetyl-S-[Epo-Fc-amido-(6-aminothioacetyl)hexonyl]cys-ser-arg-arg-ala-ser-val-tyr-amide (SEQ ID NO. 6); Epo-Fc-peptide A). A 200 ul aliquot (16.8 uM; 3.4 nmol) was dialyzed against coupling buffer prior to addition to an eppendorf tube containing ~50 nmol of peptide A NHS ester. The sample was vortexed and allowed to stand at ambient temperature for 18 hrs. The formation of the peptide A-modified Epo-Fc was demonstrated by $^{32}PO_3$-labeling as shown below.

Erythropoietin-murine-Fc-[$^{32}PO_3$]peptide A conjugate (N-α-acetyl-S-[Epo-Fc-amido-(6-aminothioacetyl)hexonyl] cys-ser-arg-arg-ala-[$^{32}PO_3$] phophoser-val-tyr-amide (SEQ ID NO. 7); Epo-Fc-[$^{32}PO_3$] peptide A). A 20 ul reaction containing 6.6 ul of the above reaction mixture (~110 pmol Epo-Fc-peptide A), 50U PKA, 20 pmol ATP (1 uM), 6.6 pmol [g-$^{32}P$]ATP (0.33 uM, 1500 Ci/mmol), 5 ul of a 50% slurry of Protein A sepharose in kinase buffer was allowed to proceed at 37° C. for 2 hr. The specific activity of this ATP/[g-$^{32}P$]ATP mixture was ~744 cpm/fmol. The resin was washed three times with TBS, pH 8 and the labeled protein eluted with 20 ul of 0.1 M citrate, pH 3. The eluted protein was neutralized with 1/10 volume 1M Tris, pH 8.0. The protein was analyzed on a 10–20% Tris-glycine acrylamide gel.

Erythropoietin-murine-Fc-[$^{33}PO_3$]peptide A conjugate (N-α-acetyl-S-[Epo-Fc-8-amido-(6-aminothioacetyl) hexonyl]cys-ser-arg-arg-ala-[$^{33}PO_3$]phosphoser-val-tyr-amide (SEQ ID NO. 7); Epo-Fc-[$^{32}PO_3$] peptide A). A 20 ul reaction containing 6.6 ul of the peptide A-labeling reaction mixture (~110 pmol Epo-Fc-peptide A, 5 uM), 50U PKA, 200 pmol ATP (10 uM), 6.6 pmol [g-$^{33}P$]ATP (0.33 uM, 1600 Ci/mmol), 5 ul of a 50% slurry of Protein A sepharose in kinase buffer was allowed to proceed at 37° C. for 2 hr. The specific activity of this ATP/[g-$^{33}P$]ATP mixture was 112 cpm/fmol. The resin was washed three times with TBS, pH 8 and the labeled protein eluted with 20 ul of 0.1 M citrate, pH 3. The eluted protein was neutralized with 1/10 volume 1M Tris, pH 8.0.

Biotin ethylenediamine-peptide A conjugate (N-α-acetyl-S-biotin-ethylenediamine-amido-(6-aminothioacetyl) hexonyl]cys-ser-arg-arg-ala-ser-val-tyr-amide (SEQ ID NO. 6); biotin-peptide A). A 116 ul aliquot of an aqueous 14 mM solution of biotin ethylenediamine hydrobromide (1.62 umol) was added to an eppendorf tube containing 50 nmol of peptide A NHS ester, followed by addition of 12 ul of 10× coupling buffer. The solution was vortexed and allowed to stand for 18 hrs. after which time the product was purified from unreacted biotin ethylenediamine by reverse phase HPLC, condition A; $t_r$ (biotin ethylenediamine) 11 min., $t_r$ (biotin-peptide A) 25 min. ES-MS m/z, 711.5 (M+2H$^+$), 1421.0 amu (calculated), 1421.4 amu (predicted).

Biotin ethylenediamine-[$^{33}PO_3$]peptide A conjugate (N-α-acetyl-S-[biotin-ethylenediamine-amido-(6-aminothioacetyl)hexonyl] cys-ser-arg-arg-ala-[$^{33}PO_3$] phosphoser-val-tyr-amide (SEQ ID NO. 7); biotin-[$^{33}PO_3$] peptide A). A 100 ul reaction containing 100 pmol of biotin-peptide A (1 uM), 100U PKA, 0.25 nmol [g-$^{33}P$]ATP (2.5 uM, 1600 Ci/mmol) in kinase buffer was allowed to proceed at 37° C. for 2 hr. The specific activity of this ATP/[g-$^{33}P$]ATP mixture was ~3552 cpm/fmol. The phosphorylated product was separated from the non-incorporated [g-$^{33}P$]ATP on reverse phase HPLC, condition A; $t_r$ ([g-$^{33}P$] ATP) ~4 min.; $t_r$ (biotin-[$PO_3$]peptide A) 23.4 min. ES-MS, (m/z, observed) 751.2 (M+2H+), 1500.4 amu (calculated), 1501.3 amu (predicted).

1-(o-3-(2-aminoethyl)sulfoxypropylphenoxy)-3-isopropylamino)-2-propanol (alprenolol amine). To 20 ul of an aqueous solution of 50 mM alprenolol was added 20 ul of an aqueous 100 mM solution of 2-aminopropane thiol and ~5 mg of potassium persulfate. The reaction was warmed to 37° C. and allowed to proceed for ~18 hours after which time an aliquot of the product was purified from unreacted alprenolol by reverse phase HPLC, condition B; $t_r$ (alprenolol) 21 min., $t_r$ (alprenolol amine) 13.4 min. ES-MS m/z, 343.3 (M+H$^+$), 342.3 amu (observed), 342.2 amu (predicted).

Alprenolol amine-peptide A conjugate (N-α-acetyl-S-[alprenololamido-(6-aminothioacetyl)hexonyl]cys-ser-arg-arg-ala-ser-val-tyr-amide; alprenolol amine-peptide A). A 60 ul aliquot of an aqueous 1 mM solution of alprenolol amine (60 nmol) was added to an eppendorf tube containing ~85 nmol of peptide A NHS ester, followed by addition of 6 ul of 10× coupling buffer. The solution was vortexed and allowed to stand for 18 hrs. after which time the product was purified from unreacted alprenolol amine and hydrolyzed peptide A NHS ester by reverse phase HPLC, condition B; $t_r$ (alprenolol amine) 13.4 min., $t_r$ (alprenolol amine-peptide A) 18 min. ES-MS m/z 740.2 (M+2H$^+$), 1476.4 amu (observed), 1476.8 amu (predicted).

Alprenolol amine-[$^{33}$P]peptide A conjugate (N-α-acetyl-S-[alprenolol amido-(6-aminothioacetyl)hexonyl](SEQ ID NO. 7) cys-ser-arg-arg-ala-[$^{33}$PO$_3$]phosphoser-val-tyr-amide; alprenolol amine-[$^{33}$P]peptide A). A 26 ul reaction containing 60 pmol alprenolol amine-peptide A (1 uM), 116U PKA, 0.25 nmol [γ-$^{33}$P]ATP (2.5 uM, 1600 Ci/mmol) in kinase buffer was allowed to proceed at 37° C. for 2 hr. The specific activity of this [γ-$^{33}$P]ATP was ~4440 cpm/fmol. The phosphorylated product was separated from the non-incorporated [γ-$^{33}$P]ATP on reverse phase HPLC, condition B; $t_r$ ([γ-$^{33}$P]ATP ~4 min.; $t_r$ (alprenolol amine-[PO$_3$] peptide A) ~17.6 min.

Ligand Binding Assays using Cells or Membranes. Cultured cells expressing the receptor of interest were suspended to ~1.6×10$^6$ per ml in DMEM containing 0.1% FBS. 100 ul aliquots were incubated in a 96-well U-bottom polypropylene microtiter plate (assay plate) containing the indicated ligands. After the appropriate incubation time (~1–3 hrs) cells were transferred to 1.5 ml eppendorf tubes and centrifuged at 2000 rpm (358×g) for 2 min at 6° C., supernatants aspirated and cells resuspended in 1 ml cell media and centrifuged again. The washed cells were resuspended in 20 ul of cell media and transferred to a microtiter plate, 80 ul/well of Optiphase® (Wallac, Turku, Finland) scintillation cocktail added and plates counted in a Wallac MicroBeta scintillation counter. For cells or membranes harvested by filtration, transfers from the assay plate were made directly to a Millipore 1.2 um GF/C filter plate treated or untreated with 0.3% PEI. Wells were washed with DMEM (3×100 ul) and a final wash with 100 ul water. Scintillation cocktail was added as described above.

Ligand Binding Assays in Elisa Plate Format. Costar EIA 96-well microtiter plates (assay plates) were coated with 40 ul/well of a solution of anchoring antibody (~1–5 ug/ml) or binding protein (0.1–0.5 ug/ml) in TBS and incubated overnight at 4° C. Plates were then blocked with 80 ul/well of 1% BSA/TBS for 30 min. Following removal of the blocking protein, 40 ul/well of receptor or receptor fusion protein (0.1–0.5 ug/ml) was added to the plate and incubated at ambient temperature for one hr. if an anchoring antibody step was used. The assay plate was then washed with TBS/0.01% BSA and 40 ul/well ligand at indicated concentrations was added. The assay plate was allowed to incubate at ambient temp. for ~1–3 hr. with shaking and then washed three times with TBS/0.01% Tween 20 using a Skan-Washer300 plate washer (Skatron, Sterling, Va.). Radiolabel was detected by the addition of 80 ul/well of Optiphase (Wallac, Turku, Finland) and the assay plate counted on a Wallace MicroBeta scintillation counter.

Scintillation Proximity Assays (SPA). Varying concentrations (2.5–10 mg/ml) of streptavidin coated SPA beads were incubated with varying concentrations of biotin ethylenediamine-[$^{33}$P]PKA substrate monophosphate (2.4–24 fmol; 4000–40,000 cpm/fmol) in 0.2 ml Tris-buffered saline containing 0.1% Tween-20 in a 96-well microtiter plate. After incubation for 1 hr. the plate was counted on a MicroBeta scintillation counter. Non-specific binding was measured in the presence of 1 mM biotin.

Peptide Sequencing. Edman degradation and analysis of the resulting phenylthiohydantoin (PTH) amino acids was performed.

Example 1

Preparation and Characterization of Reagent of the Invention

N-acetyl-cys((succinimidyl-6-(thioacetyl)amino) hexanoate)-ser-arg-arg-ala-ser-val-tyr-amide (SEQ ID NO. 6) (NHS ester). Coupling of the cysteine-containing PKA consensus containing peptide, [AcNH]CSRRASVY[NH$_2$] (SEQ ID NO. 6), to the heterobifunctional crosslinker, succinimidyl 6-((iodoacetyl)amino)hexanoate (SIAX), was accomplished in phosphate buffer, pH 6.0. Under conditions of excess SIAX, the sulfhydryl group of the peptide reacted specifically and completely with the iodoacetyl moiety of the cross linker to form the thioether conjugate, which we abbreviate herein as "NHS ester". The ester was purified by reverse phase HPLC and quantified by comparison to the 280 nm absorbance of a N-acetyl-tyrosine ethyl ester standard. The composition of the NHS ester was confirmed by electrospray mass spectrometry (ESI-MS).

Example 2

Phosphorylation of Proteins Having Varying Molecular Weights

Figure 2A:
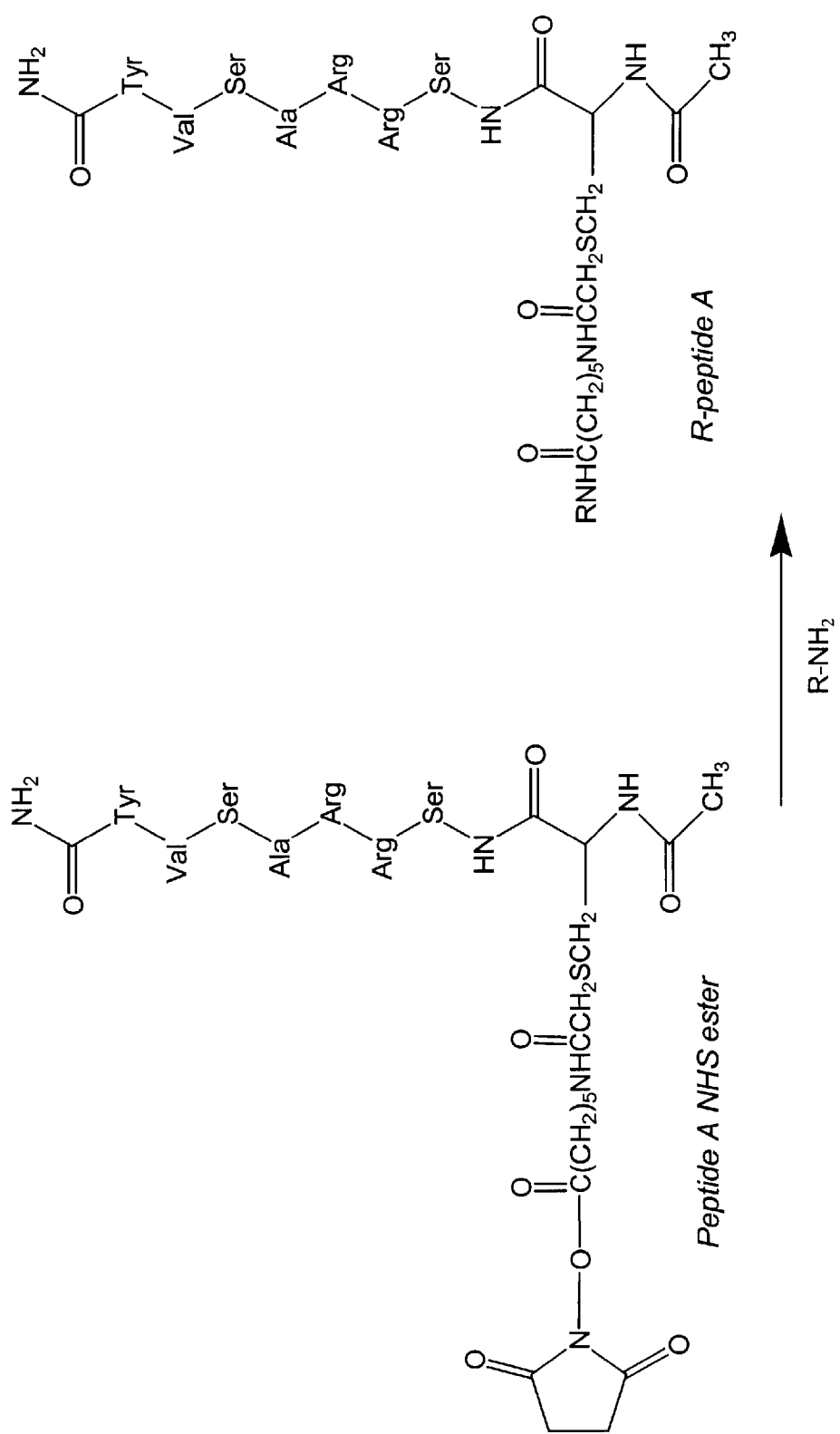
FIG. 2 shows a protein (R) modified with the reagent of the invention, and then enzymatically phosphorylated with [g-$^{32}$P]ATP using the catalytic subunit of cAMP dependent protein kinase A (PKA).
Figure 2B:
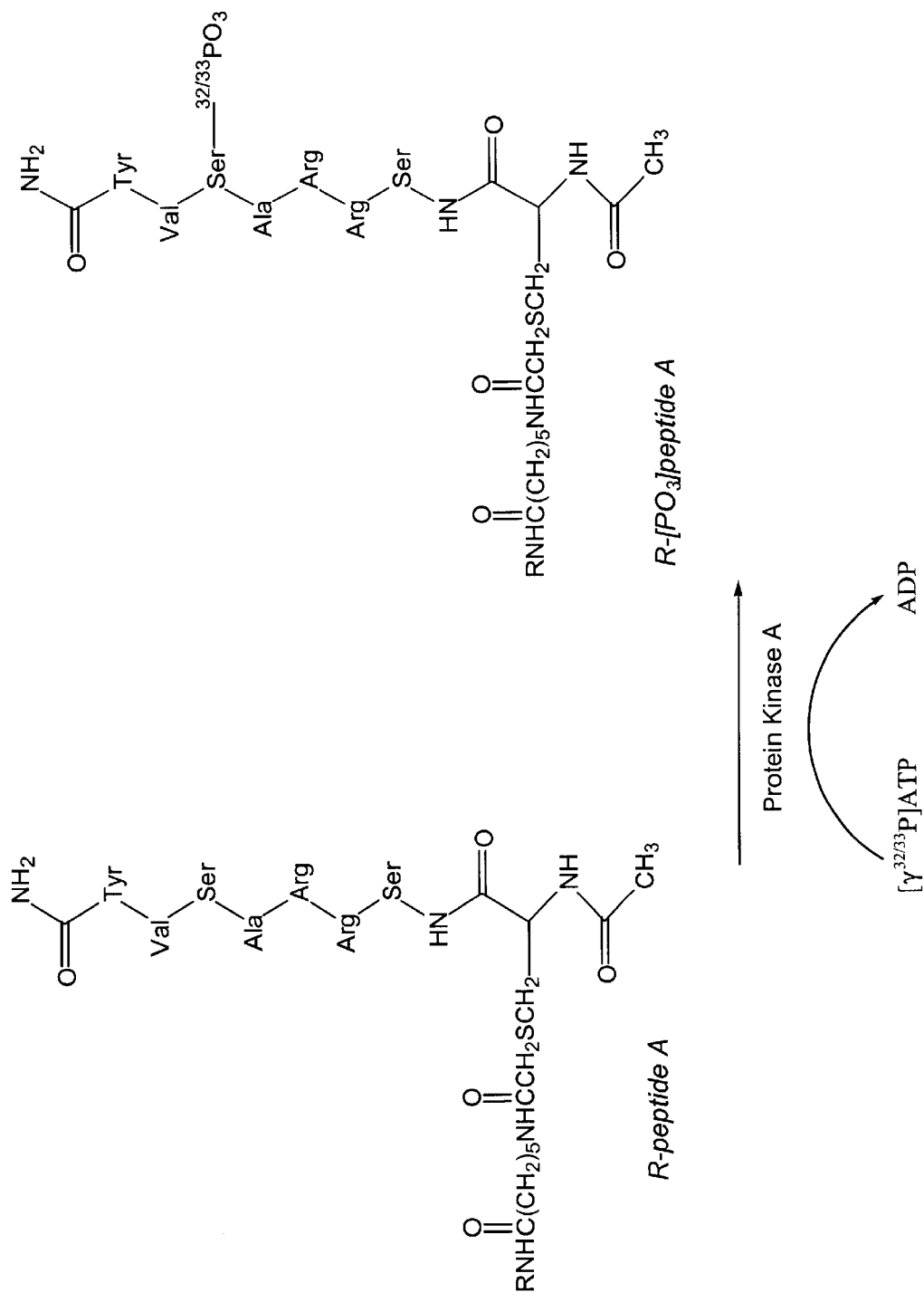

The reagent of the invention was used to modify several proteins of varying molecular weight, in particular cytochrome C, glutathione S-transferase, Aldolase, and BSA. The modified proteins were then enzymatically phosphorylated (see FIG. 2) with [g-$^{32}$P]ATP using the catalytic subunit of cAMP dependent protein kinase A (PKA). As a control, protein samples that were not treated with NHS ester were also subjected to the phosphorylation reaction. Specifically, proteins were prepared as 25 uM solutions in coupling buffer. NHS ester (10 ul of ~450 uM) was added to 45 ul aliquots of each protein to give a final volume of 55 ul per reaction and allowed to stand overnight at room temperature. The ratio of the reagent of the invention to protein was ~5:1 mole:mole. Samples were enzymatically phosphorylated by incubating 20 ul of the above coupling reaction or a mock reaction containing no reagent of the invention as described above. FIG. 1A shows a coomassie stained gel of proteins either treated (lanes 2, 4, 6, 8) or untreated (lanes 1, 3, 5, 7) with the reagent of the invention and phosphorylated with PKA using [γ-$^{32}$P]ATP. The gel lanes are as follows: (PKA is indicated by the arrowhead) 1 and 2, cytochrome C; 3 and 4, glutathione s-transferase; 5 and 6, aldolase; 7 and 8, BSA. FIG. 1B shows an autoradiograph of the same gel to detect [$^{32}$P] incorporation.

The autoradiograph of the SDS-PAGE analysis of the phosphorylated proteins (FIG. 1B) shows that all of the proteins treated with the reagent of the invention incorporated [$^{32}$P], while those not treated did not incorporate any radiolabel. These results demonstrate that modification of various proteins with the reagent of the invention covalently introduced new phosphorylation sites.

Example 3

Preparation of Phosphate Labeled Ligands

Labeling of G protein-coupled receptor ligands and cytokine receptor ligands with the reagent of the invention.

Several ligands for commonly studied receptor families, G protein-coupled receptors (GPCRs) and cytokine receptors were labeled using the reagent of the invention. Specifically, neurokinin A (NKA) was phosphorylated according to the invention and tested for binding with the NK-2 receptor, and interleukin-8 (IL8) was phosphorylated and tested for binding with the CXC2 receptor (CXCR2). The NK2 and CXC2 receptors employed in the binding studies were recombinantly expressed in CHO cells and studied in a whole cell and/or membrane binding assay format, as described in Example 4.

A derivative of the small molecule alprenolol, an antagonist of the $\beta_2$-adrenergic receptor, was coupled to the reagent of the invention and, as described in Example 4, studied in receptor binding assays. $\beta_2$-adrenergic receptor was expressed in CHO cells and sf9 cells.

The cytokine receptor for erythropoietin was studied as a recombinant soluble Fc-fusion protein containing the extracellular domain of the erythropoietin receptor fused to the Fc region of human IgG. The ligand for this receptor, erythropoietin (Epo) was also prepared as an Fc-fusion, specifically as a fusion to the Fc region of mouse IgG. This Fc-fusion of Epo was phosphorylated according to the method of invention as described above.

The cytokine receptor for leptin, the Ob receptor (ObR), was studied as a soluble Fc-fusion protein containing the extracellular domain of the ObR fused to the Fc region of human IgG (R&D Systems, Minneapolis, Minn.). The ligand for this receptor, leptin (R&D Systems) was phosphorylated according to the method of invention as described above.

In addition, a small molecule, biotin ethylenediamine, was coupled to the reagent of the invention and studied in both plate binding and homogeneous assay formats.

Peptide-$[^{33}P]$labeled ligand

Figure 3:
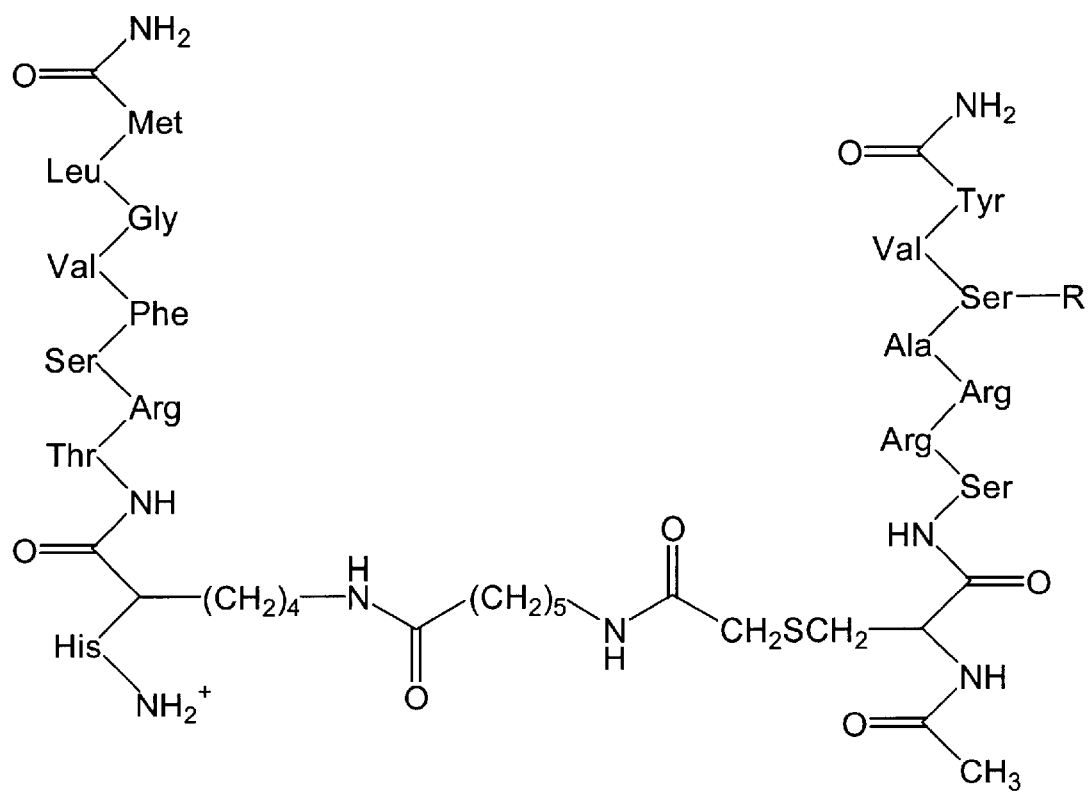
FIG. 3 shows phosphorylated neurokinin (NKA) according to the invention. The phosphorylated product (R=PO$_3$) and unphosphorylated precursor (R=H) are shown.

Neurokinin-lys$_2$N$^e$-$[^{33}P]$phosphopeptide A conjugate. Neurokinin (NKA), a decapeptide having the sequence His-lys-thr-arg-ser-phe-val-gly-leu-met-NH$_2$ (SEQ ID NO. 8) (Patacchini and Maggi (1995) *Arch. Int. Pharmacodyn. Ther.*, 329(1), 161–84) was readily modified by the NHS ester reagent of the invention under conditions of NKA excess to generate a mono-labeled product. The phosphorylated product (R=PO$_3$) and unphosphorylated precursor (R=H) are shown in FIG. 3. The NKA conjugate was purified by HPLC and characterized by ES-MS. Acylation occurred on the e-amino group of lysine2 as determined by Edman degradation analysis. The NKA-peptide A conjugate acquired a 280 nm absorbance due to the tyrosine of the peptide A sequence, which was used to quantify the conjugate by direct comparison with a tyrosine-containing standard.

Phosphorylation of the NKA-peptide A conjugate with PKA using ATP/[g-$^{33}$P]ATP and purification on reverse phase HPLC (condition B) gave the phosphorylated moiety shown in FIG. 3. The reverse phase HPLC retention time of the phosphorylated product was approximately 0.5 min. longer than the unphosphorylated compound and was confirmed to be the phosphorylation product by ESI-MS and specific activity (~13 cpm/fmol). Approximately 14% of the input ATP was turned over, as determined from the distribution of counts in the two major radioactive HPLC peak fractions.

Protein-$[^{33}P]$labeled ligand

Figure 4:
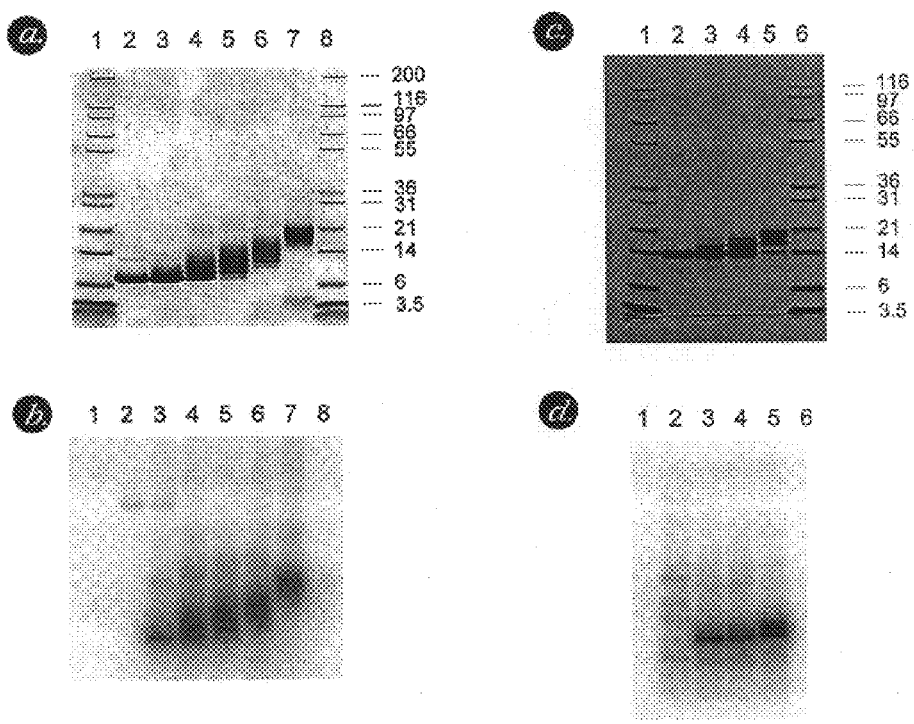
FIG. 4A shows a coomassie stained gel of an SDS-PAGE analysis of compounds modified using the reagent of the invention.
FIG. 4B shows an autoradiograph of lanes corresponding to those in FIG. 4A.
FIG. 4C shows a coomassie stained gel of an SDS-PAGE analysis of leptin that was modified using the reagent of the invention.
FIG. 4D shows an autoradiograph of lanes corresponding to those in of FIG. 4C.

Interleukin-8-$[^{33}P]$phosphopeptide A conjugate. Interleukin-8 (IL8), a 72 amino acid chemokine (Baggiolini, M. et al. (1997) *Annu. Rev. Immunol.* 15: 675–705) was chemically modified under conditions of excess NHS ester reagent of the invention. The modified protein, purified on HPLC, eluted as a slightly broader peak compared to unmodified IL8 with the same retention time. SDS-PAGE analysis and ESI-MS of the modified IL8 are shown in FIG. 4A. The lanes shown in FIG. 4A are as follows: Lane 1 and 8, lane 2, IL8, molecular weight markers; lanes 3 through 7, IL8-conjugated to varying concentrations of the reagent of the invention. Lane 5 is representative of IL8 modified by the reagent of the invention in this experiment. Samples were separated on a 14–20% NuPage gel using MOPS running buffer. Proteins were visualized with Coomassie blue.

These results showed that at least four species of modified IL8 (see Lane 5) were formed, which represent modification stoichiometries of IL8:labeling reagent of 1:1, 1:2, 1:3 and 1:4. The mass spectrum of the HPLC-purified peak resolved a series of multiple charge states corresponding to the parent masses of 9518, 10653, 11788 and 12923 amu respectively. These masses are predicted by the various IL8:labeling reagent stoichiometries. This result is consistent with the presence of at least four modifiable amines in the polypeptide sequence.

The IL8 conjugates were phosphorylated with PKA using ATP/[g-$^{33}$P]ATP and separated from the remaining [g-$^{33}$P]ATP by HPLC (condition B). The specific activity of this material was estimated to be ~100 cpm/fmol ESI-MS analysis of the HPLC-purified IL8-$[^{33}P]$ phosphate peak revealed a series of the expected multiple phosphorylation states, primarily, IL8-[PO$_3$]reagent, 9598 amu, IL8-[PO$_3$]$_2$reagent$_2$, 10813 amu and IL8-[PO$_3$]$_3$reagent$_3$, 12028 amu. However IL8-[PO$_3$]$_4$reagent$_4$ was not detected, presumably because of either a loss in the ability to form the protonated species due to phosphate modification, or because this was in relatively low abundance as indicated in the mass spectra of the starting material and SDS-PAGE gel.

Leptin-$[^{33}P]$phosphopeptide A conjugate.

Leptin, the product of the obese (OB) gene, is an adipose tissue-derived factor consisting of 146 amino acids having a four-helix bundle structure related to the family of long-chain cytokines, (e.g., G-CSF, LIF, GH and CNTF). Commercially available recombinant human leptin was modified with the NHS ester of the invention under a series of labeling stoichiometries which resulted in a ladder of labeled leptin species similar to those obtained for IL8, as revealed by SDS-PAGE analysis (FIG. 4C). As with labeling of IL8 according to the invention, the HPLC results for any one of these reactions was characterized by a peak broader than that of the unmodified cytokine and had an unchanged retention time. The leptin conjugates were phosphorylated with PKA and ATP/[γ-$^{33}$P]ATP and separated from the remaining ATP by HPLC (condition C). The specific activity of this material was estimated to be ~135 cpm/fmol.

Fusion protein-$[^{33}P]$labeled ligand

Figure 5:
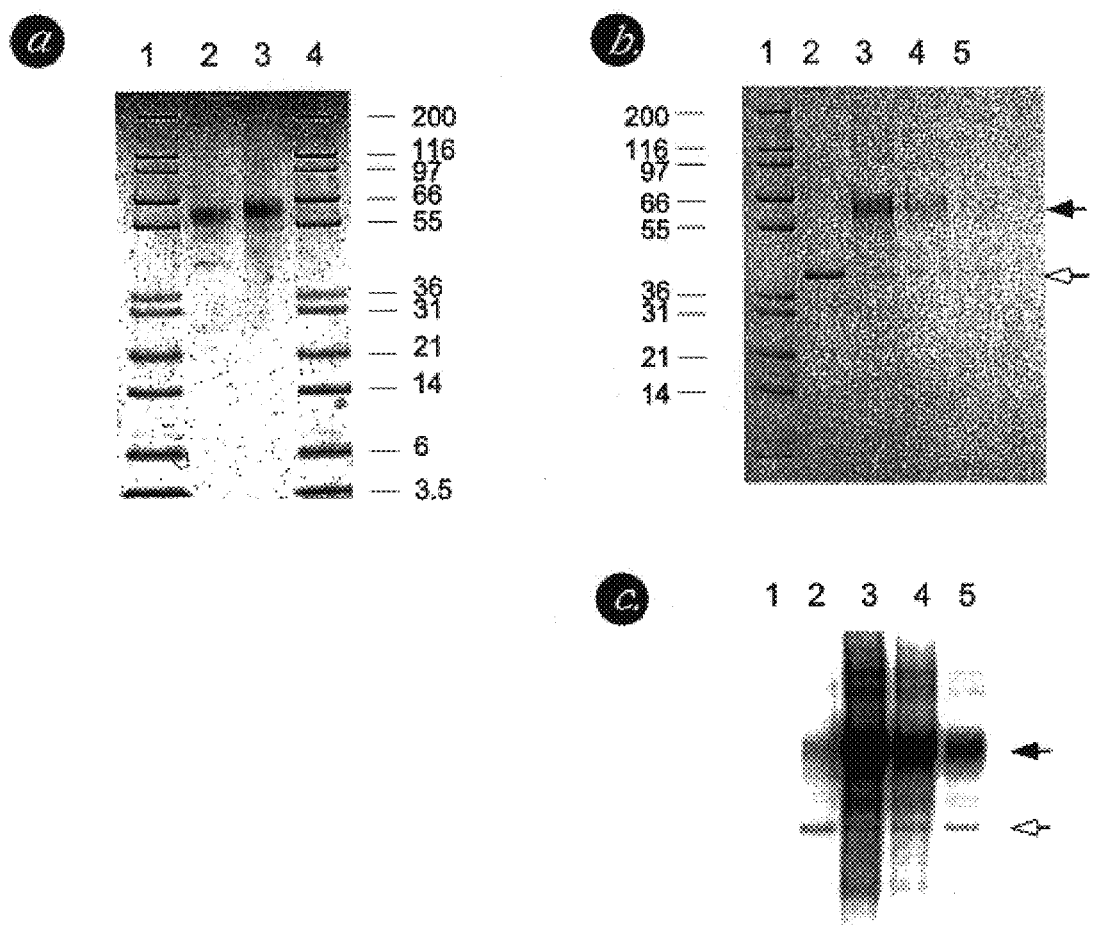
FIG. 5A shows an SDS-PAGE analysis of an Fc-fusion of erythropoietin (Epo) that was modified using the reagent of the invention.
FIG. 5B shows a coomassie stained gel of an SDS-PAGE analysis of $^{32}$P-labeled Epo-Fc.
FIG. 5C shows an autoradiograph of lanes that correspond to those in FIG. 5B.

Erythropoietin-Fc-$[^{33}P]$phosphate PKA substrate. The Fc-fusion of the 193 amino acid glycoprotein cytokine, Epo (Nicola Editor, Guidebook to Cytokines and Their Receptors (Oxford Univ. Press, NY, 1994)), was chemically modified under conditions of NHS ester reagent excess. Characterization of this material by SDS-PAGE showed that the modified Epo-Fc had a gel mobility slightly slower than unmodified Epo-Fc as might be expected due to an increase in mass. The results of this analysis are shown in FIG. 5A. The lanes shown in FIG. 5A are as follows: Lane 1 and 4, molecular weight markers; lane 2, Epo-Fc; lane 3, Epo-Fc peptide A conjugate. In this analysis, samples were separated on a 10–20% NuPage gel using Tris running buffer, and proteins were visualized with Coomassie blue.

This material was subsequently phosphorylated by PKA using ATP/[γ-$^{32}$P]ATP or ATP/[γ-$^{33}$P]ATP and purified on Protein A sepharose beads. For the $^{32}$P-labeled Epo-Fc, phosphorylation was indicated by the migration of an isotopically labeled protein of M$_r$=~60 kDa from the beads eluted with 100 mM citrate, pH 3.0. The results are shown in FIGS. 5B and 5C. FIG. 5B shows lanes as follows: Lane 1, molecular in weight markers; lane 2 supernatant from reaction (protein unbound to Protein A Sepharose); lane 3, citrate eluate, $1^{st}$ pass; lane 4, citrate eluate, $2^{nd}$ pass; lane 5, proteins left on beads after citrate elution. Samples were separated on a 10–20% NuPage gel using TRIS running buffer. Proteins were visualized with Coomassie blue (solid arrow, $^{32}$P labeled Epo-Fc; open arrow, PKA). FIG. 5C shows the same lanes as in FIG. 5B, but exposed to a PhosphorImager screen to detect $^{32}$P.

Small molecule [$^{33}$P]labeled ligand

Figure 6:
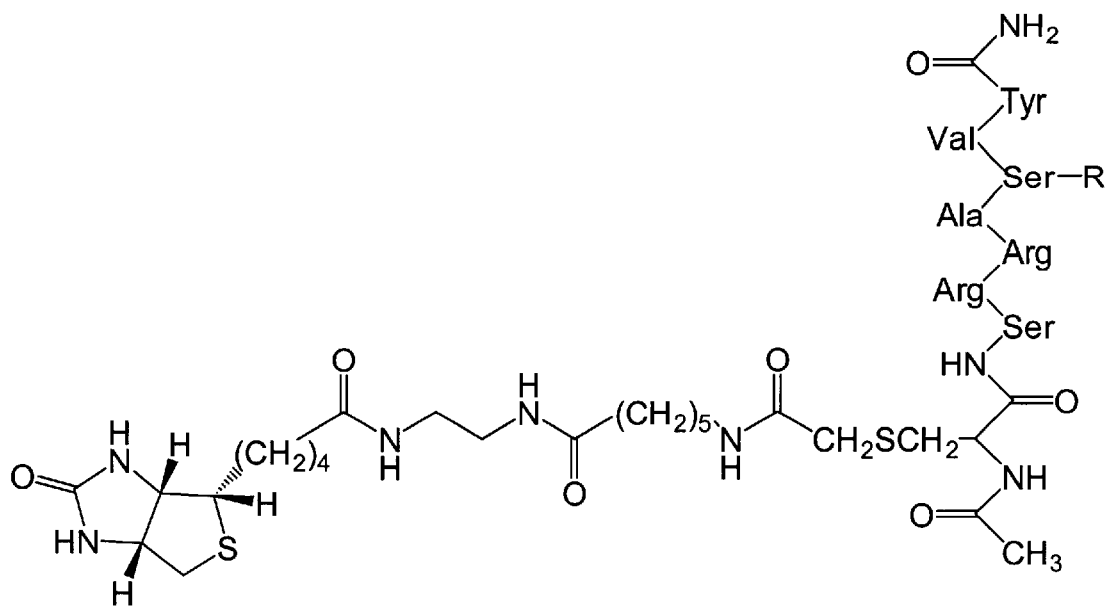
FIG. 6 shows an ethylenediamine derivative of biotin modified with the reagent of the invention.

Biotin ethylenediamine-[$^{33}$P] monophosphate PKA substrate. The ethylenediamine derivative of biotin was modified with NHS ester reagent of the invention and phosphorylated to high specific activity by PKA using [γ-$^{33}$P]ATP (3552 cpm/fmol) to give the reagent shown in FIG. 6, which was purified by HPLC (condition A). The radioactive peak corresponding to biotin ethylenediamine labeled with [$^{33}$P] monophosphate was confirmed by ESI-MS.

Alprenolol amine-[$^{33}$P]phosphopeptide A conjugate.

Alprenolol is a small molecule antagonist of the $\beta_2$-adrenergic receptor having the structure shown in FIG. 7A. A derivative of alprenolol containing a primary amine was prepared by free radical coupling with thioethylamine to give the alprenolol amine shown in FIG. 7B. This compound was modified with the NHS ester of the invention as described above to give the alprenolol amine-peptide A conjugate shown in FIG. 7C where R=H. This product was phosphorylated with PKA and [γ-$^{33}$P]ATP to high specific activity and separated from the remaining ATP by HPLC (condition B).

Example 4

Binding Studies

Receptor binding studies using [$^{33}$P]labeled ligands. Binding studies were carried out to determine whether each of the [$^{33}$PO$_3$]labeled ligands of the invention could bind specifically to its cognate receptor. For the GPCR ligands (labeled NKA, IL-8, and alprenolol), it was determined whether the ligands bound specifically to cells expressing the appropriate receptor, for the cytokine ligand (labeled Epo-Fc) a microtiter plate surface coated with the ligand-binding domain of the receptor was used, while the small molecule, biotin, was tested in SPA format. By estimating the signal expected from ligands of known specific activities and approximate receptor numbers per cell, saturating concentrations of NKA-[$^{33}$P] phosphate reagent of the invention and IL8-[$^{33}$P]phosphate reagent of the invention were incubated with CHO cells expressing either the NK2 receptor (Garland et al. (1996) Mol. Pharmacol. 49(3), 438–46) or the CXC2 receptor (Inglese (1998, supra)). Epo-Fc-[$^{33}$P] phosphate PKA substrate was incubated with an Fc-fusion of the extracellular domain of the erythropoietin receptor coated on the surface of a 96-well microtiter plate. Biotin ethylenediamine-[$^{33}$P]monophosphate reagent of the invention was incubated with streptavidin-coated SPA beads or NeutrAvidin immobilized to the surface of a 96-well microtiter plate.

FIG. 8 shows binding results for three G protein-coupled receptor ligands labeled with $^{33}$P according to the invention: NKA, IL8 and an alprenolol derivative. The results in FIG. 8 show that each labeled ligand bound specifically to its receptor or binding protein identifying binding site numbers in the expected ranges (i.e., in the low fmol range).

Saturation binding experiments provided the data shown in FIG. 9. Specifically, FIG. 9A shows results for saturation binding of NKA-[$^{33}$P]phosphopeptide A to NK2 receptors (160,000 cells/assay), $B_{max}$=700,000 receptors/cell. FIG. 9B shows results for saturation binding of IL8-[$^{33}$P] phosphopeptide A to CXC2 receptors (160,000 cells/assay), $B_{max}$=110,000 receptors/cell. FIG. 9C shows results for saturation binding of Epo-Fc-[$^{33}$P]phosphopeptide A to EpoR-Fc surface-coated plates; ~20 Fmol/well was detected at the highest concentration of Epo-Fc-[$^{33}$P]phosphopeptide A.

FIG. 9D shows saturation binding of leptin [$^{33}$P] phosphopeptide A to Obr-Fc surface-coated plates. Binding was detected at the highest concentration of leptin-[$^{33}$P] phosphopeptide A.

In the table shown in FIG. 10, the estimated dissociation constants for four of the ligands studied are compared with those of the corresponding $^{125}$I- or Eu$^{3+}$-labeled ligands. The references cited in the Figure are as follows: Burcher et al., Eur. J Pharmacol. 128:165–177; Lee et al., (1986) Eur. J. Pharmacol. 130:209–217; Inglese et al., Biochemistry, 37:2372–2377; Wrighton et al., (1996) Science 273:458–464; Appell et al., (1998) Biomolecular Screening, 3:19–27; Tartaglia et al., (1995) Cell 83:1263–1271; Fong et al., (1998) Mol. Pharmacol. 53:234–240. "sEPOR" in the Figure legend refers to soluble EPO receptor.

Figure 11B:
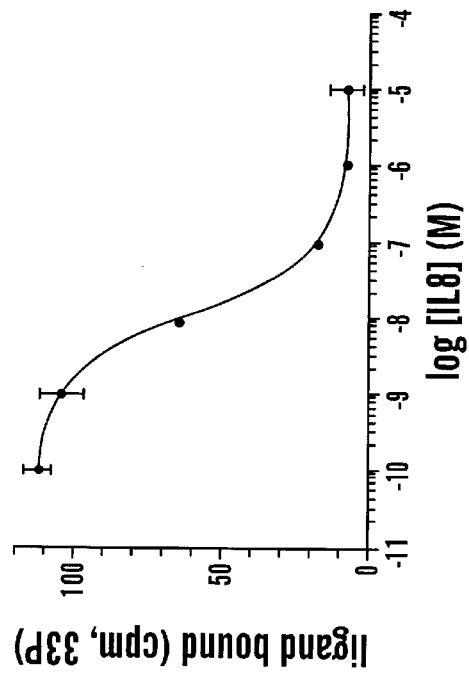
FIG. 11B shows a binding plot for competition of IL8-[$^{33}$P]labeled ligand of the invention for CXC2 receptor on CHO cells.
Figure 11D:
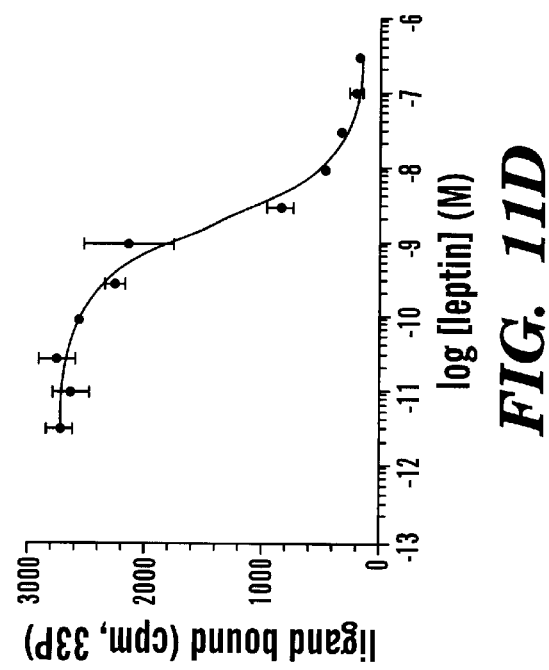
FIG. 11D shows a binding plot for competition of leptin [$^{33}$P]labeled ligand of the invention for ObR-Fc surface-coated plates.
Figure 11A:
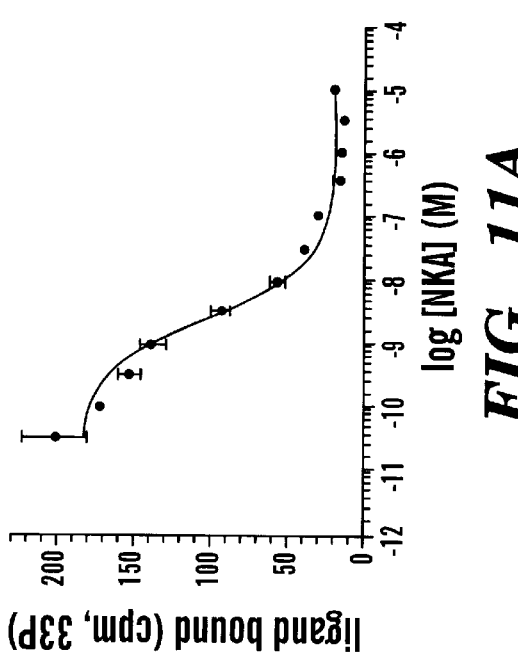
FIG. 11A shows a binding plot for competition of NKA-[$^{33}$P]labeled ligand of the invention by NKA for NK2 receptor on CHO cells.
Figure 11C:
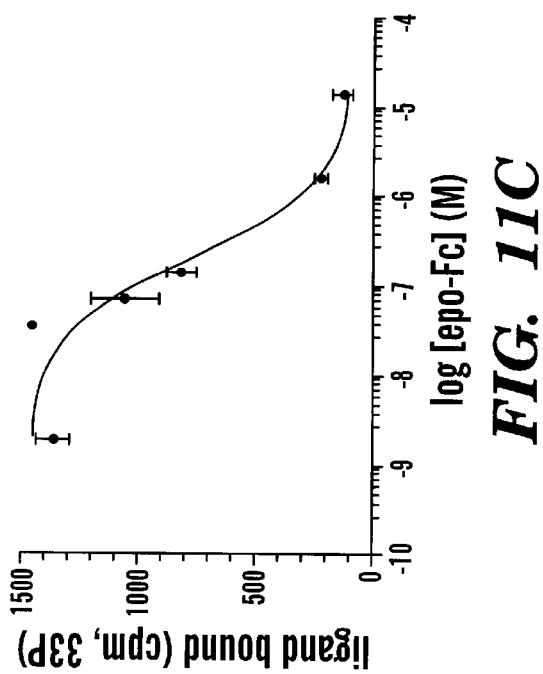
FIG. 11C shows a binding plot for competition of Epo-[$^{33}$P]labeled ligand of the invention for EpoR-Fc surface-coated plates.

[$^{33}$P]labeled ligands of the invention were also used as tracers in competition binding experiments. Specifically, FIG. 11A shows results for competition of 33 nM NKA-[$^{33}$P]phosphopeptide A by NKA for NK2 receptors on CHO cells using PEI-coated GF/C-filter bottom microtiter plates. FIG. 11B shows results for competition of 50 nM IL8-[$^{33}$P] phosphopeptide A by IL8 for CXC2 receptors on CHO cells. FIG. 11C shows results for competition of 20 nM Epo-Fc-[$^{33}$P]phosphopeptide A by Epo-Fc for EpoR-Fc surface-coated plates. FIG. 11D shows results for competition of 2 nm leptin [$^{33}$P]phosphopeptide A by leptin for ObR-Fc surface-coated plates.

The results in FIGS. 10 and 11 indicate that the $K_i$s for unlabeled ligands, competing with [$^{33}$P]labeled ligands for receptor binding, are similar to those reported in competition assays using $^{125}$I- and Eu$^{3+}$-labeled ligands.

We claim:

1. A reagent for incorporation of a phosphorylation site by reaction with a free primary or secondary amine in a compound to be phosphorylated, said reagent comprising a substituted or unsubstituted succinimidyl moiety linked to a kinase substrate.

2. The reagent of claim 1 wherein said succinimidyl moiety is unsubstituted.

3. The reagent of claim 1 wherein said succinimidyl moiety of said reagent is subtituted by an SO$_3$Na group.

4. The reagent of claim 1 wherein said kinase substrate comprises the sequence SRRASVY (SEQ ID NO. 1).

5. The reagent of claim 1 wherein said succinimidyl moiety is linked to said kinase substrate through linkage of a cysteine thiol located at the amino terminus of the kinase substrate with an acetamide moiety conjugated through a linker region to said succinimidyl moiety.

6. A reagent for incorporation of a phosphorylation site by reaction with a free primary or secondary amine in a compound to be phosphorylated, said reagent comprising the structure

A—B—C wherein A is an N-hydroxysuccinimide ester, B is a linking group, and C is a peptide sequence that comprises a kinase substrate.

7. A reagent according to claim 6 wherein C is an N-acetyl cysteinyl peptide including a sequence that comprises a kinase substrate, said N-acetyl cysteinyl peptide being covalently attached to said linking group through the cysteinyl sulfur.

8. A reagent according to claim 6 wherein said reagent has a structure selected from the group consisting of:

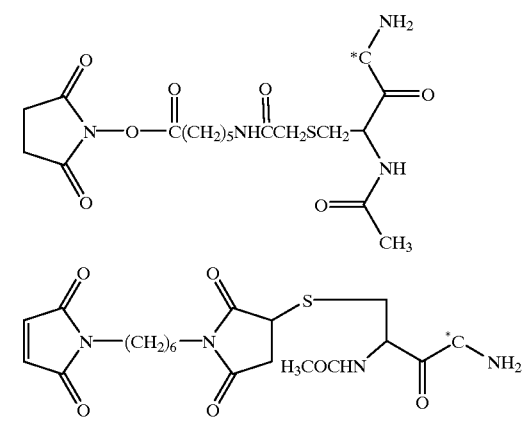

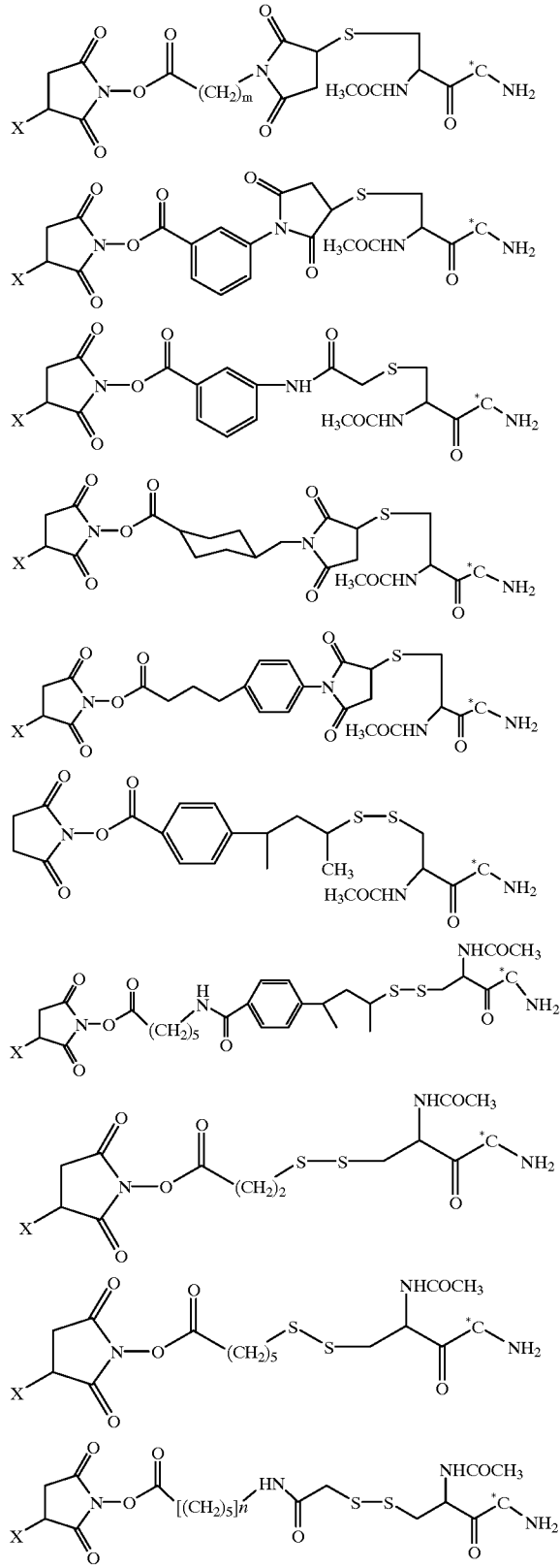

wherein C* is the peptide sequence SRRASVY (SEQ ID NO.1), X is H or SO₃; m is selected from 3 to 5, and n is selected from 1 and 2.

9. A reagent according to claim 8 having the structure

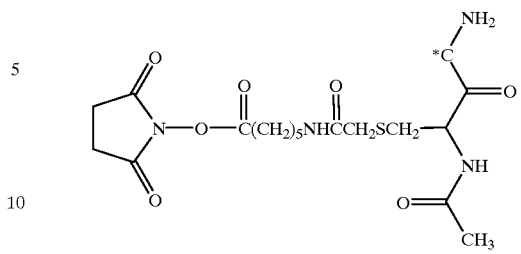

wherein C* is the peptide sequence SRRASVY (SEQ ID NO.1).

10. A reagent for incorporation of a phosphorylation site by reaction with a reactive side chain of a compound to be phosphorylated, said reagent comprising the structure

A—B—C wherein A is a moiety that is specifically reactive with said reactive side chain; C is a peptide sequence that comprises a kinase substrate; and B is a linkinig moiety, wherein said linking moiety is selected from bismaleimidohexane, 1,4-di-[3-(2-pryidyldithio)-propionamido)]butane, N-γ-maleimidobutyryloxy-succinimide ester, N-γ-maleimidobutyryloxysulfosuccinimide ester, m-maleimidobenzoyl-N-hydroxysuccinimide ester, N-hydroxysuccinimidyl-2,3-dibromopropionate, m-maleimidobenxoyl-N-hydroxysulfosuccinimide ester, N-succinimidyl[4-iodoacetyl]aminobenzoate, sulfosuccinimidyl[4-iodoacetyl]aminobenzoate, succinimidyl 4-[N-maleimidomethyl]cyclohexane-1-carboxylate, sulfosuccinimidyl-4[N-maleimidomethyl]cyclohexane-1-carboxylate, succinimidyl 4-[p-maleimidophenyl]butyrate, sulfosuccinimidyl 4-[p-maleimidophenyl]butyrate, 4-succinimidyloxycabonylmethyl-α-[2-pyridyldithio] toluene, sulfosuccinimidyl-6-[α-methyl-α-(2-pyridyldithio) toluamido]hexanoate, N-succinimidyl-3-[2-pyridyldithio] propionate, succinimidyl 6-[3-(2-pyridyldithio) propionamido]hexanoate, sulfosuccinimidyl 6-[3-(2-pyridyldithio)propionamido]hexanoate, succinimidyl 6-[(iodoacetyl)amino]hexanoate and succinimidyl 6-[6-[[(iodoacetyl)amino]hexanoyl]amino]hexanoate.

11. A reagent for incorporation of a phosphorylation site by reaction with an amine in a compound to be phosphorylated, said reagent comprising the structure

A—B—C wherein A is an isothiocyanate, B is a linking group, and C is a peptide sequence that comprises a kinase substrate.

12. A reagent for incorporation of a phosphorylation site by reaction with a thiol in a compound to be phosphorylated, said reagent comprising the structure

A—B—C wherein A is a pyridyl disulfide, B is a linking group, and C is a peptide sequence that comprises a kinase substrate.

13. A method of phosphorylation comprising reacting the reagent of claim 6 with said compound of claim 6 and then phosphorylating the resulting product using a protein kinase under phosphorylating conditions.

14. The method of claim 13 comprising phosphorylating with $^{32}$P-phosphate.

15. The method of claim 13 comprising phosphorylating with $^{33}$P-phosphate.

16. The method of claim 13 wherein said compound is a protein or polypeptide.

* * * * *

SEQUENCE LISTING

<160> NUMBER OF SEQ ID NOS: 8

<210> SEQ ID NO 1
<211> LENGTH: 7
<212> TYPE: PRT
<213> ORGANISM: Artificial Sequence
<220> FEATURE:

```
<223> OTHER INFORMATION: Description of Artificial Sequence:Designed
      peptide to act as kinase substrate

<400> SEQUENCE: 1

Ser Arg Arg Ala Ser Val Tyr
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:Designed
      peptide to act as kinase substrate

<400> SEQUENCE: 2

Leu Arg Arg Ala Ser Leu Gly
 1               5

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:Designed
      peptide to act as kinase substrate

<400> SEQUENCE: 3

Lys Val Glu Lys Ile Gly Glu Gly Thr Tyr Gly Val Val Tyr Lys
 1               5                  10                  15

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence:Designed
      peptide to act as kinase substrate
<220> FEATURE:
<221> NAME/KEY: MOD_RES
<222> LOCATION: (1)
<223> OTHER INFORMATION: PYRROLIDONE CARBOXYLIC ACID

<400> SEQUENCE: 4

Glu Gly Pro Trp Leu Glu Glu Glu Glu Ala Tyr Gly Trp Met Asp
 1               5                  10                  15

Phe

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:Designed
      peptide to act as kinase substrate

<400> SEQUENCE: 5

Arg Arg Leu Ile Glu Asp Ala Glu Tyr Ala Ala Arg Gly
 1               5                  10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:Designed
      peptide to act as kinase substrate
<220> FEATURE:
```

```
<221> NAME/KEY: MOD_RES
<222> LOCATION: (1)
<223> OTHER INFORMATION: ACETYLATION

<400> SEQUENCE: 6

Cys Ser Arg Arg Ala Ser Val Tyr
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:Designed
      peptide to act as kinase substrate
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (6)
<223> OTHER INFORMATION: PHOSPHORYLATION

<400> SEQUENCE: 7

Cys Ser Arg Arg Ala Ser Val Tyr
 1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:Designed
      peptide to act as kinase substrate

<400> SEQUENCE: 8

His Lys Thr Arg Ser Phe Val Gly Leu Met
 1               5                  10
```